(12) United States Patent
Konetzki et al.

(10) Patent No.: US 7,423,035 B2
(45) Date of Patent: Sep. 9, 2008

(54) SUBSTITUTED CYCLOALKYL DERIVATIVES, PROCESS FOR THE MANUFACTURE THEREOF AND USE THEREOF AS MEDICAMENT

(75) Inventors: Ingo Konetzki, Warthausen (DE); Thierry Bouyssou, Mietingen (DE); Philipp Lustenberger, Warthausen (DE); Andreas Schnapp, Biberach (DE); Christoph Hoenke, Ingelheim (DE); Klaus Rudolf, Warthausen (DE); Marco Santagostino, Magenta (IT)

(73) Assignee: Boehringer Ingelheim International GmbH, Ingelheim (DE)

( * ) Notice: Subject to any disclaimer, the term of this patent is extended or adjusted under 35 U.S.C. 154(b) by 258 days.

(21) Appl. No.: 11/125,757

(22) Filed: May 10, 2005

(65) Prior Publication Data

US 2005/0261286 A1 Nov. 24, 2005

Related U.S. Application Data

(60) Provisional application No. 60/578,568, filed on Jun. 10, 2004.

(30) Foreign Application Priority Data

May 13, 2004 (EP) .................................. 04425343

(51) Int. Cl.
*C07D 265/36* (2006.01)
*A61K 31/538* (2006.01)
*A61K 31/138* (2006.01)

(52) U.S. Cl. ..................................... 514/230.5; 544/105
(58) Field of Classification Search .................. 544/105; 514/230.5

See application file for complete search history.

(56) References Cited

U.S. PATENT DOCUMENTS 3,081,336 A 3/1963 Kaiser et al.
4,270,002 A 5/1981 Kirino et al.

FOREIGN PATENT DOCUMENTS

GB 973887 10/1964

WO 9533724 A1 12/1995

OTHER PUBLICATIONS

Vippagunta et al, "Crystalline Solids" Advanced Drug Delivery Reviews, vol. 48, pp. 3-26 (2001).*
GavezzotU, "Are Crystal Structures Predictable?" Accounts of Chemical Research, vol. 27, pp. 309-314 (1994).*
Temple et al.; Adrenergic Sulfonanilides. 4. Centrally Active beta-adrenergic agonists; Journal of Medicinal Chemistry; 1976; vol. 19; No. 5; pp. 626-633.
International Search Report, Form PCT/ISA/210, for corresponding PCT/EP2005/005025 (2005).
Airapetyan et al.; Isoquinoline derivatives. XXVI. Synthesis of N-arylalkanol derivatives of 4-spiro-substituted 1,2,3,4-tethydroisoquinolines and 1-(3,4-dimethoxyphenyl)-1-cycloalkylmethylamines with beta-adrenoblocking properties; Database Chemabs; Chemical Abstracts Service; Columbus, OH; 1988; Database accession No. 1988:37609; abstract only.
Bertus et al.; Ti(II)-Mediated Conversion of a-Heterosubstituted (O, N, S) Nitriles to Functionalized Cyclopropylamines. Effect of Chelation on the Cyclopropanation Step; Journal of Organic Chemistry; 2002; vol. 67; pp. 3965-3968.
Hass et al.; Carbon Aralkylations of Nitro Paraffins: Journal of Organic Chemistry; 1949; vol. 71; pp. 2290-2291.

* cited by examiner

*Primary Examiner*—Kahsay T Habte
(74) *Attorney, Agent, or Firm*—Michael P. Morris; Mary-Ellen M. Devlin

(57) ABSTRACT

The present invention relates to compounds of formula 1

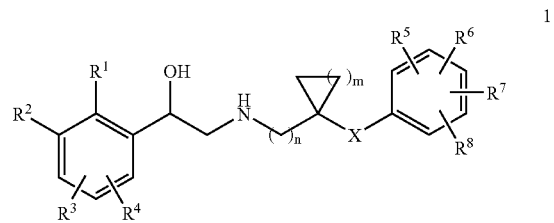

wherein the groups $R^1$, $R^2$, $R^3$, $R^4$, $R^5$, $R^6$, $R^7$, $R^8$, n, m and X may have the meanings given in the claims and in the specification, and the use thereof as pharmaceutical compositions, particularly for the treatment of inflammatory and obstructive respiratory complaints.

14 Claims, No Drawings

SUBSTITUTED CYCLOALKYL DERIVATIVES, PROCESS FOR THE MANUFACTURE THEREOF AND USE THEREOF AS MEDICAMENT

This application claims priority under 35 USC 119(e) to U.S. Provisional Application 60/578,568, filed Jun. 10, 2004.

The present invention relates to compounds of formula 1

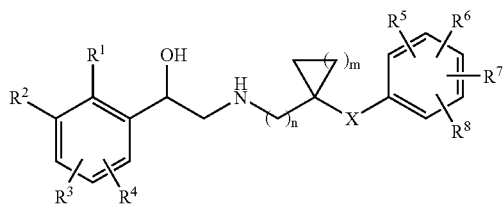

wherein the groups $R^1$, $R^2$, $R^3$, $R^4$, $R^5$, $R^6$, $R^7$, $R^8$, n, m and X may have the meanings given in the claims and in the specification, and the use thereof as pharmaceutical compositions, particularly for the treatment of inflammatory and obstructive respiratory complaints.

BACKGROUND TO THE INVENTION

Betamimetics (β-adrenergic substances) are known from the prior art (WO9533724; J. Med. Chem. 1976, 9, 626). For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which are characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. A further objective of the invention is to prepare new betamimetics which, by virtue of their long-lasting effect, can be used to prepare a drug for administration once a day for the treatment of inflammatory or obstructive respiratory complaints. In addition to the objectives mentioned above a further aim of the present invention is to prepare betamimetics which are not only exceptionally potent but are also characterised by a high degree of selectivity with respect to the β2-adrenoceptor.

DESCRIPTION OF THE INVENTION

Surprisingly it has been found that the above-mentioned objectives are achieved by compounds of formula 1. Accordingly, the present invention relates to compounds of formula 1

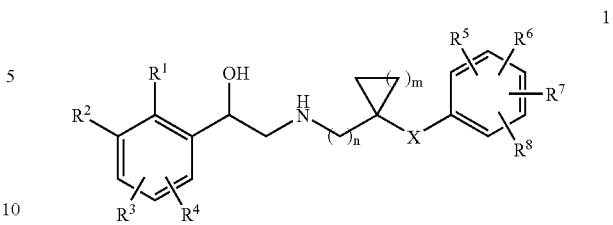

wherein
n denotes 0 or 1;
m denotes 1, 2, 3 or 4;
X denotes a single bond or one of the double-bonded groups $C_2$-$C_6$-alkenylene, —O—$C_1$-$C_6$-alkylene, —NH—$C_1$-$C_6$-alkylene, —S—$C_1$-$C_6$-alkylene or $C_1$-$C_6$-alkylene;
$R^1$ denotes hydrogen;
$R^2$ denotes —$C_1$-$C_4$-hydroxyalkyl or halogen, or
$R^1$ and $R^2$ together denote a double-bonded group selected from —O—$CH_2$—C(O)—NH, —$CH_2$—$CH_2$—C(O)—NH, —CH=CH—C(O)—NH, —NH—$CH_2$—C(O)—NH, —S—$CH_2$—C(O)—NH, —O—C(O)—NH, —S—C(O)—NH, —NH—C(O)—NH, and —O—$CH_2$—$SO_2$-NH, wherein in each case one or 2 hydrogen atoms may be replaced by one or two groups selected from among —$C_1$-$C_4$-alkyl, OH, or halogen;
$R^3$ and $R^4$ which may be identical or different denote a group selected from among hydrogen, OH, halogen, —$C_1$-$C_6$-alkyl, —$C_1$-$C_6$-haloalkyl, —$C_1$-$C_6$-hydroxyalkyl, $NH_2$, NH(—$C_1$-$C_4$-alkyl) and N(—$C_1$-$C_4$-alkyl)$_2$;
$R^5$, $R^6$, $R^7$ and $R^8$, which may be identical or different, denote hydrogen, $OR^9$, —$C_1$-$C_6$-alkyl, —$C_1$-$C_6$-haloalkyl, —$C_1$-$C_6$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$ or halogen, or
two of the groups $R^5$, $R^6$, $R^7$ and $R^8$, if they are located vicinally to the substituting phenyl ring, together form a double-bonded group selected from $C_2$-$C_6$-alkylene, $C_2$-$C_6$-alkenylene and —O—$C_1$-$C_6$-alkylene-O— wherein in each case one or 2 hydrogen atoms may be replaced by one or two groups selected from among —$C_1$-$C_4$-alkyl, —$C_1$-$C_4$-alkoxy, OH, or halogen;
$R^9$ denotes hydrogen, $C_1$-$C_4$-alkyl, $C_6$-$C_{10}$-aryl or $C_6$-$C_{10}$-aryl-$C_1$-$C_4$-alkylene;
$R^{10}$ and $R^{11}$ which may be identical or different, denote hydrogen, $C_1$-$C_4$-alkyl, $C_6$-$C_{10}$-aryl or $C_6$-$C_{10}$-aryl-$C_1$-$C_4$-alkylene;
$R^{12}$ denotes $C_1$-$C_4$-alkyl, $C_6$-$C_{10}$-aryl or $C_6$-$C_{10}$-aryl-$C_1$-$C_4$-alkylene, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1, wherein
n denotes 0 or 1;
m denotes 1, 2, 3 or 4;
X denotes a single bond or one of the double-bonded groups $C_2$-$C_4$-alkenylene, —O—$C_1$-$C_4$-alkylene, —NH—$C_1$-$C_4$-alkylene, —S—$C_1$-$C_4$-alkylene or $C_1$-$C_4$-alkylene;

$R^1$ denotes hydrogen;

$R^2$ denotes —$CH_2$—$CH_2$—OH, —$CH_2$—OH, fluorine, chlorine or bromine or $R^1$ and $R^2$ together denote a double-bonded group selected from —O—$CH_2$—C(O)—NH, —$CH_2$—$CH_2$—C(O)—NH, —CH=CH—C(O)—NH, —NH—$CH_2$—C(O)—NH, —O—C(O)—NH, —NH—C(O)—NH— and —O—$CH_2$—$SO_2$—NH, wherein in each case one or 2 hydrogen atoms may be replaced by one or two groups selected from among methyl, OH, fluorine, chlorine, or bromine;

$R^3$ and $R^4$ which may be identical or different denote a group selected from among hydrogen, OH, halogen, —$C_1$-$C_4$-alkyl, —$C_1$-$C_4$-haloalkyl, —$C_1$-$C_4$-hydroxyalkyl, $NH_2$, NH(—$C_1$-$C_4$-alkyl) and N(—$C_1$-$C_4$-alkyl)$_2$;

$R^5$, $R^6$, $R^7$ and $R^8$, which may be identical or different, denote hydrogen, $OR^9$, —$C_1$-$C_4$-alkyl, —$C_1$-$C_4$-haloalkyl, —$C_1$-$C_4$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$, fluorine, chlorine or bromine, or two of the groups $R^5$, $R^6$, $R^7$ and $R^8$, if they are located vicinally to the substituting phenyl ring, together form a double-bonded group selected from $C_2$-$C_4$-alkylene, $C_2$-$C_4$-alkenylene and —O—$C_1$-$C_4$-alkylene-O— wherein in each case one or 2 hydrogen atoms may be replaced by one or two groups selected from among methyl, methoxy, OH, fluorine, chlorine or bromine;

$R^9$ denotes hydrogen, methyl, ethyl, phenyl, naphthyl, benzyl, naphthylmethyl or 2-phenylethyl;

$R^{10}$ and $R^{11}$ which may be identical or different, denote hydrogen, methyl, ethyl, phenyl, naphthyl, naphthylmethyl, benzyl or 2-phenylethyl;

$R^{12}$ denotes methyl, ethyl, phenyl, naphthyl, naphthylmethyl, benzyl or 2-phenylethyl;

optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of general formula 1, wherein n denotes 0 or 1;

m denotes 1, 2, 3 or 4;

X denotes a single bond or one of the double-bonded groups —$CH_2$, —$CH_2$—$CH_2$, —$CH_2$—$CH_2$—$CH_2$, —CH=CH, —$CH_2$—CH=CH, —$CH_2$—O, —$CH_2$—$CH_2$—O, —$CH_2$—$NH_2$, —$CH_2$—$CH_2$—$NH_2$—;

$R^1$ denotes hydrogen;

$R^2$ denotes —$CH_2$—$CH_2$—OH, —$CH_2$—OH, fluorine, chlorine or bromine or $R^1$ and $R^2$ together denote a double-bonded group selected from —O—$CH_2$—C(O)—NH, —$CH_2$—$CH_2$—C(O)—NH, —CH=CH—C(O)—NH, or —O—C(O)—NH, wherein in each case one or 2 hydrogen atoms may be replaced by one or two groups selected from among methyl, OH, fluorine, chlorine, or bromine, preferably methyl;

$R^3$ and $R^4$ which may be identical or different denote a group selected from among hydrogen, OH, fluorine, chlorine, bromine, methyl, ethyl, —$CH_2$F, —$CHF_2$, —$CF_3$, —$CH_2$—$CH_2$—OH, —$CH_2$—OH, $NH_2$, NH(methyl) and N(methyl)$_2$;

$R^5$, $R^6$, $R^7$ and $R^8$, which may be identical or different, denote hydrogen, OH, methyl, ethyl, propyl, butyl, —$CH_2$F, —$CHF_2$, —$CF_3$, —$CH_2$—$CH_2$F, —$CH_2$—$CHF_2$, —$CH_2$—$CF_3$, —$CH_2$—$CH_2$—OH, —$CH_2$—OH, cyclpropyl, cyclobutyl, cyclopentyl, HO-cyclopropyl, HO-cyclobutyl, HO-cyclopentyl, —CN, $NO_2$, —COphenyl, —COOmethyl, —COOethyl, —$CONH_2$, —CONHmethyl, —CONHphenyl, —CONHbenzyl, —CON(methyl)$_2$, $NH_2$, NH(methyl), N(methyl)$_2$, —NHCOmethyl, —NHCOphenyl, —$NHSO_2$methyl, —$NHSO_2$phenyl, —$NHSO_2$-phenyl-$CH_3$, —$SO_2$methyl, —$SO_2$-phenyl, —$SO_2$-phenyl-$CH_3$, —$SO_2NH_2$, fluorine, chlorine or bromine, or two of the groups $R^5$, $R^6$, $R^7$ and $R^8$, if they are located vicinally to the substituting phenyl ring, together form a double-bonded group selected from —$CH_2$—$CH_2$—$CH_2$, —$CH_2$—$CH_2$—$CH_2$—$CH_2$, —$CH_2$—CH=CH, —CH=CH—CH=CH, —O—$CH_2$—O— and —O—$CH_2$—$CH_2$—O— wherein in each case one or 2 hydrogen atoms may be replaced by one or two groups selected from among methyl, methoxy, OH or fluorine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of formula 1, wherein

X denotes a single bond or one of the double-bonded groups —$CH_2$, —$CH_2CH_2$, —$CH_2$—O, preferably a single bond or one of the double-bonded groups —O—$CH_2$— and —$CH_2$, particularly preferably —$CH_2$, and wherein the groups $R^1$, $R^2$, $R^3$, $R^4$, $R^5$, $R^6$, $R^7$, $R^8$, n and m may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein $R^1$ denotes hydrogen;

$R^2$ denotes methyl, ethyl, $CHF_2$, $CH_2F$, $CF_3$, —$CH_2$—$CH_2$—OH, —$CH_2$—OH, fluorine, chlorine or bromine, or $R^1$ and $R^2$ together denote a double-bonded group selected from —O—$CH_2$—C(O)—NH, —$CH_2$—$CH_2$—C(O)—NH, —CH=CH—C(O)—NH— and —CH=CH—CH=CH, and wherein the groups $R^3$, $R^4$, $R^5$, $R^6$, $R^7$, $R^8$, n, m and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein $R^3$ and $R^4$ which may be identical or different denote a group selected from among hydrogen, OH, fluorine, chlorine, bromine, methyl, ethyl, $CHF_2$, $CH_2F$, $CF_3$, —$CH_2$—$CH_2$—OH, —$CH_2$—OH, $NH_2$, NHmethyl, NHethyl, N(methyl)$_2$ and N(ethyl)$_2$, preferably selected from among hydrogen, OH, fluorine, $CH_2F$, $CF_3$ and $NH_2$, and wherein the groups $R^1$, $R^2$, $R^5$, $R^6$, $R^7$, $R^8$, n, m and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
$R^5, R^6, R^7$ and $R^8$, which may be identical or different, denote hydrogen, OH, methyl, ethyl, propyl, butyl, $CHF_2$, $CH_2F$, $CF_3$, $—CH_2—CH_2—OH$, $—CH_2—OH$, methyloxy, ethyloxy, propyloxy, butyloxy, cyclopropyl, hydroxycyclopropyl, $NH_2$, NHmethyl, N(methyl)$_2$, fluorine, chlorine or bromine, or
  two of the groups $R^5$, $R^6$, $R^7$ and $R^8$ if they are located vicinally to the substituted phenyl ring, together denote the double-bonded group —CH=CH—CH=CH— wherein in each case one or 2 hydrogen atoms may be replaced by one or two groups selected from among methyl, methoxy, OH, fluorine, chlorine or bromine, and wherein the groups $R^1$, $R^2$, $R^3$, $R^4$ n, m and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
$R^5, R^6, R^7$ and $R^8$, which may be identical or different, denote hydrogen, OH, methyl, ethyl, propyl, butyl, $CHF_2$, $CH_2F$, $CF_3$, methyloxy, ethyloxy, propyloxy, butyloxy, cyclopropyl, hydroxycyclopropyl, $NH_2$, fluorine, chlorine or bromine, and wherein the groups $R^1$, $R^2$, $R^3$, $R^4$ n, m and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
$R^5, R^6, R^7$ and $R^8$, which may be identical or different, denote hydrogen, OH, methyl, $CF_3$, methyloxy, ethyloxy, propyloxy, butyloxy, hydroxycyclopropyl, $NH_2$, fluorine or chlorine, and wherein the groups $R^1$, $R^2$, $R^3$, $R^4$ n, m and X may have the above-mentioned meanings, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
$R^5$ and $R^8$ denotes hydrogen;
$R^6$ and $R^7$ if they are located vicinally to the substituting phenyl ring, together denote the double-bonded group —CH=CH—CH=CH—, and wherein the groups $R^1$, $R^2$, $R^3$, $R^4$ n, m and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
n denotes 0;
m denotes 2, and wherein the groups $R^1$, $R^2$, $R^3$, $R^4$, $R^5$, $R^6$, $R^7$, $R^8$ and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Also particularly preferred are compounds of formula 1, wherein
n denotes 0;
m denotes 3, and wherein the groups $R^1$, $R^2$, $R^3$, $R^4$, $R^5$, $R^6$, $R^7$, $R^8$ and X may have the meanings given hereinbefore, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

In a preferred aspect the present invention relates to compounds of general formula 1, wherein
n denotes 0 or 1, preferably 0;
m denotes 1, 2, 3 or 4, preferably 1;
X denotes a single bond or one of the double-bonded groups —$CH_2$—, —$CH_2CH_2$—, —$CH_2$—O, preferably a single bond or one of the double-bonded groups —O—$CH_2$— and —$CH_2$, particularly preferably —$CH_2$,
$R^1$ denotes hydrogen and
$R^2$ denotes —$CH_2$—OH, or
  $R^1$ and $R^2$ together denote a double-bonded group selected from —O—$CH_2$—C(O)—NH, —$CH_2$—$CH_2$—C(O)—NH, —CH=CH—C(O)—NH, —NH—$CH_2$—C(O)—NH, —S—$CH_2$—C(O)—NH, —O—C(O)—NH, —NH—C(O)—NH, and —O—$CH_2$—$SO_2$—NH;
$R^3$ denotes hydrogen;
$R^4$ denotes OH, and wherein the groups $R^5$, $R^6$, $R^7$ and $R^8$ may have the meanings given above, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1, wherein
$R^5, R^6, R^7$ and $R^8$, which may be identical or different, denote hydrogen, $OR^9$, —$C_1$-$C_4$-alkyl, —$C_1$-$C_4$-haloalkyl, —$C_1$-$C_4$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$, fluorine, chlorine or bromine, or two of the groups $R^5, R^6, R^7$ and $R^8$, if they are located vicinally to the substituting phenyl ring, together form a double-bonded group selected from
  $C_2$-$C_4$-alkylene, $C_2$-$C_4$-alkenylene and —O—$C_1$-$C_4$-alkylene-O— wherein in each case one or 2 hydrogen atoms may be replaced by one or two groups selected from among methyl, methoxy, OH, fluorine, chlorine or bromine;

$R^9$ denotes hydrogen, methyl, ethyl, phenyl, naphthyl, benzyl, naphthylmethyl or 2-phenylethyl;

$R^{10}$ and $R^{11}$ which may be identical or different, denote hydrogen, methyl, ethyl, phenyl, naphthyl, naphthylmethyl, benzyl or 2-phenylethyl;

$R^{12}$ denotes methyl, ethyl, phenyl, naphthyl, naphthylmethyl, benzyl or 2-phenylethyl, and wherein the groups $R^1$, $R^2$, $R^3$, $R^4$, n, m and X may have the meanings given above, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

A preferred group of compounds according to the invention are compounds of general formula 1 wherein the groups $R^1$ and $R^2$ together form the double-bonded group —O—CH$_2$—C(O)—NH— and the groups $R^3$, $R^4$, $R^5$, $R^6$, $R^7$ $R^8$, n, m and X may have the meanings given above.

Preferred regioisomers of this group may be represented by general formula 1a

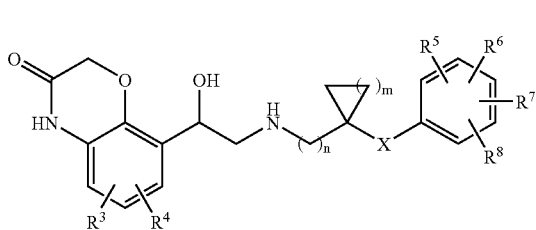

1a

In a preferred aspect the present invention relates to compounds of general formula 1a, wherein n denotes 0 or 1, preferably 0;

m denotes 1, 2, 3 or 4, preferably 1;

X denotes a single bond or one of the double-bonded groups —CH$_2$, —CH$_2$CH$_2$, —CH$_2$—O, preferably a single bond or one of the double-bonded groups —O—CH$_2$— and —CH$_2$, particularly preferably —CH$_2$, $R^3$ denotes hydrogen;

$R^4$ denotes OH;

$R^5$, $R^6$, $R^7$ and $R^8$, which may be identical or different, denote hydrogen, OR$^9$, —C$_1$-C$_4$-alkyl, —C$_1$-C$_4$-haloalkyl, —C$_1$-C$_4$-hydroxyalkyl, —C$_3$-C$_6$-cycloalkyl, —C$_3$-C$_6$-hydroxycycloalkyl, —CN, NO$_2$, —COR$^9$, —COOR$^9$, —CONR$^{10}$R$^{11}$, —NR$^{10}$R$^{11}$, —NR$^{10}$COR$^9$, —NR$^{10}$SO$_2$R$^{12}$, —SR$^{12}$, —SOR$^{12}$, —SO$_2$R$^{12}$, —SO$_2$NR$^{10}$R$^{11}$, fluorine, chlorine or bromine, or two of the groups $R^5$, $R^6$, $R^7$ and $R^8$, if they are located vicinally to the substituting phenyl ring, together form a double-bonded group selected from C$_2$-C$_4$-alkylene, C$_2$-C$_4$-alkenylene and —O—C$_1$-C$_4$-alkylene-O— wherein in each case one or 2 hydrogen atoms may be replaced by one or two groups selected from among methyl, methoxy, OH, fluorine, chlorine or bromine;

$R^9$ denotes hydrogen, methyl, ethyl, phenyl, naphthyl, benzyl, naphthylmethyl or 2-phenylethyl;

$R^{10}$ and $R^{11}$ which may be identical or different, denote hydrogen, methyl, ethyl, phenyl, naphthyl, naphthylmethyl, benzyl or 2-phenylethyl;

$R^{12}$ denotes methyl, ethyl, phenyl, naphthyl, naphthylmethyl, benzyl or 2-phenylethyl, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1a, wherein n denotes 0 or 1, preferably 0;

m denotes 1, 2, 3 or 4, preferably 1;

X denotes a single bond or one of the double-bonded groups —CH$_2$, —CH$_2$—CH$_2$, —CH$_2$—CH$_2$—CH$_2$, —CH═CH, —CH$_2$—CH═CH, —CH$_2$—O, —CH$_2$—CH$_2$—O, —CH$_2$—NH$_2$, —CH$_2$—CH$_2$-NH$_2$—;

$R^3$ denotes hydrogen;

$R^4$ denotes hydrogen, fluorine, methyl, OH or CF$_3$, preferably OH;

$R^5$ and $R^8$ which may be identical or different, denote hydrogen, methyl, methyloxy or fluorine;

$R^6$ and $R^7$ which may be identical or different, denote hydrogen, OH, methyl, ethyl, CF$_3$, methyloxy, ethyloxy, propyloxy, butyloxy, cyclopropyl, hydroxycyclopropyl, NH$_2$ or fluorine, or $R^6$ and $R^7$, if they are located vicinally to the substituting phenyl ring, together form the double-bonded group —CH═CH—CH═CH— wherein in each case one or 2 hydrogen atoms may be replaced by one or two groups selected from among methyl, methoxy, OH, fluorine, chlorine and bromine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1a, wherein n denotes 0 or 1, preferably 0;

m denotes 1, 2, 3 or 4, preferably 1;

X denotes a single bond or one of the double-bonded groups —CH$_2$, —CH$_2$CH$_2$, —CH$_2$—O, preferably a single bond or one of the double-bonded groups —O—CH$_2$— and —CH$_2$, particularly preferably —CH$_2$, $R^3$ denotes hydrogen;

$R^4$ denotes OH;

$R^5$ and $R^8$ which may be identical or different, denote hydrogen, methyl, methyloxy or fluorine;

$R^6$ and $R^7$ which may be identical or different, denote hydrogen, OH, methyl, CF$_3$, methyloxy, ethyloxy, propyloxy, butyloxy, hydroxycyclopropyl, NH$_2$ or fluorine, or $R^6$ and $R^7$, if they are located vicinally to the substituting phenyl ring, together form the double-bonded group —CH═CH—CH═CH, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of general formula a, wherein $R^4$ denotes OH;

$R^5$, $R^6$ and $R^8$ which may be identical or different, denote hydrogen or methyl, preferably hydrogen;

R[7] denotes hydrogen, OH, methyl, CF$_3$, methyloxy, ethyloxy, propyloxy or butyloxy, preferably OH, methyloxy, ethyloxy, propyloxy or butyloxy, and n, m, X and R[3] may have the meanings given above, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

A preferred group of compounds according to the invention are compounds of general formula 1 wherein the groups R[1] and R[2] together form the double-bonded group —CH=CH—C(O)—NH— and the groups R[3], R[4], R[5], R[6], R[7], R[8], n, m and X may have the meanings given above.

Preferred regioisomers of this group may be represented by general formula 1b

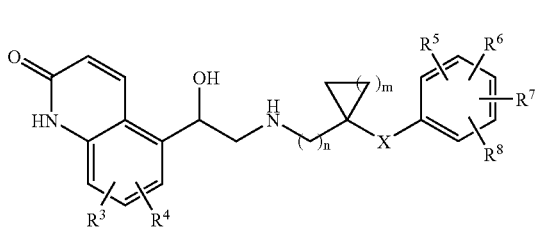

1b

In a preferred aspect the present invention relates to compounds of general formula 1b, wherein n denotes 0 or 1, preferably 0;

m denotes 1, 2, 3 or 4, preferably 1;

X denotes a single bond or one of the double-bonded groups —CH$_2$—, —CH$_2$—CH$_2$—, —CH$_2$—CH$_2$—CH$_2$—, —CH=CH—, —CH$_2$—CH=CH, —CH$_2$—O—, —CH$_2$—CH$_2$—O—, —CH$_2$—NH$_2$, —CH$_2$—CH$_2$—NH$_2$—;

R[3] denotes hydrogen;

R[4] denotes hydrogen, fluorine, methyl, OH or CF$_3$, preferably OH;

R[5] and R[8] which may be identical or different, denote hydrogen, methyl, methyloxy or fluorine;

R[6] and R[7] which may be identical or different, denote hydrogen, OH, methyl, ethyl, CF$_3$, methyloxy, ethyloxy, propyloxy, butyloxy, cyclopropyl, hydroxycyclopropyl, NH$_2$ or fluorine, or R[6] and R[7], if they are located vicinally to the substituting phenyl ring, together form the double-bonded group —CH=CH—CH=CH— wherein in each case one or 2 hydrogen atoms may be replaced by one or two groups selected from among methyl, methoxy, OH, fluorine, chlorine and bromine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1b, wherein n denotes 0 or 1, preferably 0;

m denotes 1, 2, 3 or 4, preferably 1;

X denotes a single bond or one of the double-bonded groups —CH$_2$—, —CH$_2$CH$_2$—, —CH$_2$—O, preferably a single bond or one of the double-bonded groups —O—CH$_2$— and —CH$_2$, particularly preferably —CH$_2$, R[3] denotes hydrogen;

R[4] denotes OH;

R[5] and R[8] which may be identical or different, denote hydrogen, methyl, methyloxy or fluorine;

R[6] and R[7] which may be identical or different, denote hydrogen, OH, methyl, CF$_3$, methyloxy, ethyloxy, propyloxy, butyloxy, hydroxycyclopropyl, NH$_2$ or fluorine, or R[6] and R[7], if they are located vicinally to the substituting phenyl ring, together form the double-bonded group —CH=CH—CH=CH, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of general formula 1b, wherein n denotes 0 or 1, preferably 0;

m denotes 1, 2, 3 or 4, preferably 1;

X denotes the double-bonded group —CH$_2$—;

R[3] denotes hydrogen;

R[4] denotes OH;

R[5], R[6] and R[8] which may be identical or different, denote hydrogen or methyl, preferably hydrogen;

R[7] denotes hydrogen, OH, methyl, CF$_3$, methyloxy or ethyloxy, preferably OH, CF$_3$ or methyloxy, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

A preferred group of compounds according to the invention are compounds of general formula 1 wherein R[1] denotes hydrogen, R[2] denotes chlorine, R[3] denotes NH$_2$ and R[4] denotes chlorine and the groups R[5], R[6], R[7], R[8], n, m and X may have the meanings given above. Preferred regioisomers of this group may be represented by general formula 1c

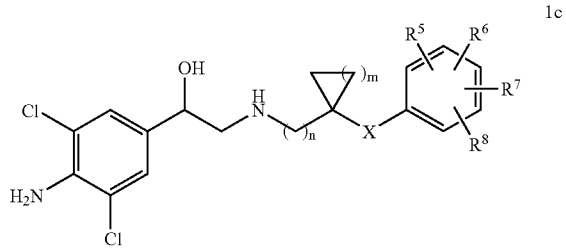

1c

In a preferred aspect the present invention relates to compounds of general formula 1c, wherein n denotes 0 or 1, preferably 0;

m denotes 1, 2, 3 or 4, preferably 1;

X denotes a single bond or one of the double-bonded groups —CH$_2$—, —CH$_2$—CH$_2$—, —CH$_2$—CH$_2$—CH$_2$—, —CH=CH—, —CH$_2$—CH=CH, —CH$_2$—O, —CH$_2$—CH$_2$—O, —CH$_2$—NH$_2$, —CH$_2$—CH$_2$—NH$_2$—;

R[5] and R[8] which may be identical or different, denote hydrogen, methyl, methyloxy or fluorine;

R[6] and R[7] which may be identical or different, denote hydrogen, OH, methyl, ethyl, CF$_3$, methyloxy, ethyloxy, propyloxy, butyloxy, cyclopropyl, hydroxycyclopropyl, NH$_2$ or fluorine, or $R^6$ and $R^7$, if they are located vicinally to the substituting phenyl ring, together form the double-bonded group —CH=CH—CH=CH— wherein in each case one or 2 hydrogen atoms may be replaced by one or two groups selected from among methyl, methoxy, OH, fluorine, chlorine and bromine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1c, wherein
n denotes 0 or 1, preferably 0;
m denotes 1, 2, 3 or 4, preferably 1;
X denotes a single bond or one of the double-bonded groups —$CH_2$—, —$CH_2CH_2$—, —$CH_2$—O, preferably a single bond or one of the double-bonded groups —O—$CH_2$— and —$CH_2$—, particularly preferably —$CH_2$—,
$R^5$ and $R^8$ denotes hydrogen;
$R^6$ and $R^7$ which may be identical or different, denote hydrogen, OH, methyl, $CF_3$, methyloxy or ethyloxy, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of general formula 1c, wherein
n denotes 0 or 1, preferably 0;
m denotes 1, 2, 3 or 4, preferably 1;
X denotes the double-bonded group —$CH_2$—;
$R^5$, $R^6$ and $R^8$ which may be identical or different, denote hydrogen or methyl, preferably hydrogen;
$R^7$ denotes hydrogen, OH, methyloxy or ethyloxy, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

A preferred group of compounds according to the invention are compounds of general formula 1 wherein $R^1$ denotes hydrogen, $R^2$ denotes hydroxymethyl and $R^3$ denotes OH and the groups $R^4$, $R^5$, $R^6$, $R^7$, $R^8$, n, m and X may have the meanings given above.

Preferred regioisomers of this group may be represented by general formula 1d

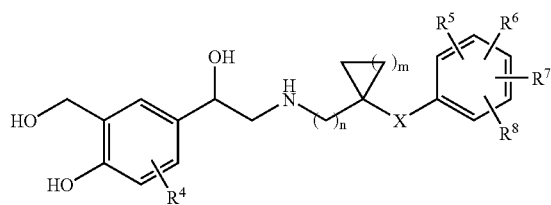

1d

In a preferred aspect the present invention relates to compounds of general formula 1d,
wherein
n denotes 0 or 1, preferably 0; m denotes 1, 2, 3 or 4, preferably 1; X denotes a single bond or one of the double-bonded groups —$CH_2$, —$CH_2$—$CH_2$, —$CH_2$—$CH_2$—$CH_2$, —CH=CH, —$CH_2$—CH=CH, —$CH_2$—O, —$CH_2$—$CH_2$—O, —$CH_2$—$NH_2$, —$CH_2$—$CH_2$—$NH_2$—;
$R^4$ denotes hydrogen, fluorine, methyl, OH or $CF_3$, preferably hydrogen;
$R^5$ and $R^8$ which may be identical or different, denote hydrogen, methyl, methyloxy or fluorine;
$R^6$ and $R^7$ which may be identical or different, denote hydrogen, OH, methyl, ethyl, $CF_3$, methyloxy, ethyloxy, propyloxy, butyloxy, cyclopropyl, hydroxycyclopropyl, $NH_2$ or fluorine, or
$R^6$ and $R^7$, if they are located vicinally to the substituting phenyl ring, together form the double-bonded group —CH=CH—CH=CH— wherein in each case one or 2 hydrogen atoms may be replaced by one or two groups selected from among methyl, methoxy, OH, fluorine, chlorine and bromine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Preferred are compounds of general formula 1 d, wherein
n denotes 0 or 1, preferably 0;
m denotes 1, 2, 3 or 4, preferably 1;
X denotes a single bond or one of the double-bonded groups —$CH_2$, —$CH_2CH_2$, —$CH_2$—O, preferably a single bond or one of the double-bonded groups —O—$CH_2$— and —$CH_2$, particularly preferably —$CH_2$,
$R^4$ denotes hydrogen;
$R^5$ and $R^8$ which may be identical or different, denote hydrogen, methyl, methyloxy or fluorine, preferably hydrogen;
$R^6$ and $R^7$ which may be identical or different, denote hydrogen, OH, methyl, $CF_3$, methyloxy, ethyloxy, propyloxy, butyloxy, $NH_2$ or fluorine, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred are compounds of general formula 1d, wherein
n denotes 0 or 1, preferably 0;
m denotes 1, 2, 3 or 4, preferably 1;
X denotes the double-bonded group —$CH_2$—;
$R^4$ denotes hydrogen;
$R^5$, $R^6$ and $R^8$ which may be identical or different, denote hydrogen or methyl, preferably hydrogen;
$R^7$ denotes hydrogen, OH, methyl, $CF_3$, methyloxy or ethyloxy, preferably OH, $CF_3$ or methyloxy, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

Particularly preferred compounds of formula 1 are selected from among:
5-hydroxy-8-{1-hydroxy-2-[1-(4-methoxy-benzyl)-cyclopropylamino]-ethyl}-4H-benzo[1,4]oxazin-3-one;
8-[2-(1-benzyl-cyclopropylamino)-1-hydroxy-ethyl]-5-hydroxy-4H-benzo[1,4]oxazin-3-one;
8-{2-[1-(2,6-dimethyl-benzyl)-cyclopropylamino]-1-hydroxy-ethyl}-5-hydroxy-4H-benzo[1,4]oxazin-3-one;
8-{2-[1-(3,4-dimethyl-benzyl)-cyclopropylamino]-1-hydroxy-ethyl}-5-hydroxy-4H-benzo[1,4]oxazin-3-one;

5-hydroxy-8-{1-hydroxy-2-[1-(3-methyl-benzyl)-cyclopropylamino]-ethyl}-4H-benzo[1,4]oxazin-3-one;
5-hydroxy-8-{1-hydroxy-2-[1-(2-trifluoromethyl-benzyl)-cyclopropylamino]-ethyl}-4H-benzo[1,4]oxazin-3-one;
5-hydroxy-8-(1-hydroxy-2-{1-[4-(1-hydroxy-cyclopropyl)-benzyl]-cyclopropylamino}-ethyl)-4H-benzo[1,4]oxazin-3-one;
8-{2-[1-(3,5-difluoro-benzyl)-cyclopropylamino]-1-hydroxy-ethyl}-5-hydroxy-4H-benzo[1,4]oxazin-3-one;
5-hydroxy-8-[1-hydroxy-2-(1-phenoxymethyl-cyclopropylamino)-ethyl]-4H-benzo[1,4]oxazin-3-one;
5-hydroxy-8-{1-hydroxy-2-[1-(4-trifluoromethyl-benzyl)-cyclopropylamino]-ethyl}-4H-benzo[1,4]oxazin-3-one;
5-hydroxy-8-{1-hydroxy-2-[1-(2-methoxy-benzyl)-cyclopropylamino]-ethyl}-4H-benzo[1,4]oxazin-3-one;
5-hydroxy-8-{1-hydroxy-2-[1-(2-methyl-benzyl)-cyclopropylamino]-ethyl}-4H-benzo[1,4]oxazin-3-one;
8-{2-[1-(2,6-dimethyl-phenoxymethyl)-cyclopropylamino]-1-hydroxy-ethyl}-5-hydroxy-4H-benzo[1,4]oxazin-3-one;
5-hydroxy-8-[1-hydroxy-2-(1-naphthalen-2-ylmethyl-cyclopropylamino)-ethyl]-4H-benzo[1,4]oxazin-3-one;
8-{2-[1-(2,4-dimethyl-benzyl)-cyclopropylamino]-1-hydroxy-ethyl}-5-hydroxy-4H-benzo[1,4]oxazin-3-one;
5-hydroxy-8-{1-hydroxy-2-[1-(2,3,5,6-tetramethyl-benzyl)-cyclopropylamino]-ethyl}-4H-benzo[1,4]oxazin-3-one;
5-hydroxy-8-(1-hydroxy-2-{1-[2-(4-methoxy-phenyl)-ethyl]-cyclopropylamino}-ethyl)-4H-benzo[1,4]oxazin-3-one;
8-{2-[1-(2,6-difluoro-benzyl)-cyclopropylamino]-1-hydroxy-ethyl}-5-hydroxy-4H-benzo[1,4]oxazin-3-one;
8-{2-[1-(4-amino-benzyl)-cyclopropylamino]-1-hydroxy-ethyl}-5-hydroxy-4H-benzo[1,4]oxazin-3-one;
5-hydroxy-8-{1-hydroxy-2-[1-(4-hydroxy-benzyl)-cyclopropylamino]-ethyl}-4H-benzo[1,4]oxazin-3-one;
8-{2-[1-(3,4-dimethoxy-benzyl)-cyclopropylamino]-1-hydroxy-ethyl}-5-hydroxy-4H-benzo[1,4]oxazin-3-one;
8-{2-[1-(4-ethoxy-benzyl)-cyclopropylamino]-1-hydroxy-ethyl}-5-hydroxy-4H-benzo[1,4]oxazin-3-one;
8-{2-[1-(4-butoxy-benzyl)-cyclopropylamino]-1-hydroxy-ethyl}-5-hydroxy-4H-benzo[1,4]oxazin-3-one;
5-hydroxy-8-{1-hydroxy-2-[1-(2,4,6-trimethyl-benzyl)-cyclopropylamino]-ethyl}-4H-benzo[1,4]oxazin-3-one;
5-hydroxy-8-{1-hydroxy-2-[(1-phenyl-cyclopropylmethyl)-amino]-ethyl}-4H-benzo[1,4]oxazin-3-one;
5-hydroxy-8-{1-hydroxy-2-[1-(2-naphthalen-2-yl-ethyl)-cyclopropylamino]-ethyl}-4H-benzo[1,4]oxazin-3-one;
2-hydroxymethyl-4-{1-hydroxy-2-[(1-phenyl-cyclopropylmethyl)-amino]-ethyl}-phenol;
4-{1-hydroxy-2-[1-(4-methoxy-benzyl)-cyclopropylamino]-ethyl}-2-hydroxymethyl-phenol;
4-[2-(1-benzyl-cyclopropylamino)-1-hydroxy-ethyl]-2-hydroxymethyl-phenol;
4-{2-[1-(2,6-dimethyl-benzyl)-cyclopropylamino]-1-hydroxy-ethyl}-2-hydroxymethyl-phenol;
6-hydroxy-8-{1-hydroxy-2-[1-(4-methoxy-benzyl)-cyclopropylamino]-ethyl}-4H-benzo[1,4]oxazin-3-one;
6-hydroxy-8-{1-hydroxy-2-[1-(4-hydroxy-benzyl)-cyclopropylamino]-ethyl}-4H-benzo[1,4]oxazin-3-one;
6-hydroxy-8-{1-hydroxy-2-[(1-phenyl-cyclopropylmethyl)-amino]-ethyl}-4H-benzo[1,4]oxazin-3-one;
8-{2-[1-(2,6-dimethyl-benzyl)-cyclopropylamino]-1-hydroxy-ethyl}-6-hydroxy-4H-benzo[1,4]oxazin-3-one;
8-{2-[1-(4-chloro-phenoxymethyl)-cyclopropylamino]-1-hydroxy-ethyl}-6-hydroxy-4H-benzo[1,4]oxazin-3-one;
1-(4-amino-3,5-dichloro-phenyl)-2-[(1-phenyl-cyclopropylmethyl)-amino}-ethanol;
1-(4-amino-3,5-dichloro-phenyl)-2-[1-(2,6-dimethyl-benzyl)-cyclopropylamino]-ethanol;
1-(4-amino-3,5-dichloro-phenyl)-2-[1-(4-methoxy-benzyl)-cyclopropylamino]-ethanol;
1-(4-amino-3,5-dichloro-phenyl)-2-(1-benzyl-cyclopropylamino)-ethanol;
8-hydroxy-5-{1-hydroxy-2-[1-(4-methoxy-benzyl)-cyclopropylamino]-ethyl}-1H-quinolin-2-one and
8-hydroxy-5-{1-hydroxy-2-[1-(4-trifluoromethyl-benzyl)-cyclopropylamino]-ethyl}-1H-quinolin-2-one, optionally in the form of the individual optical isomers, mixtures of the individual enantiomers or racemates, in the form of the free bases or the corresponding acid addition salts thereof with pharmacologically acceptable acids, and optionally in the form of the solvates or hydrates thereof.

The compounds of formula 1 may optionally be used in the form of the individual optical isomers, mixtures of the individual enantiomers or racemates. Most preferably they are used in the form of the enantiomerically pure compounds, wherein the asymmetric carbon centre "—CH(OH)—" benzylic to the phenyl ring in the compounds of formula 1 is in the R-configuration. The particularly preferred R-enantiomers of the compounds of general formula 1 may be represented by general formula R-1,

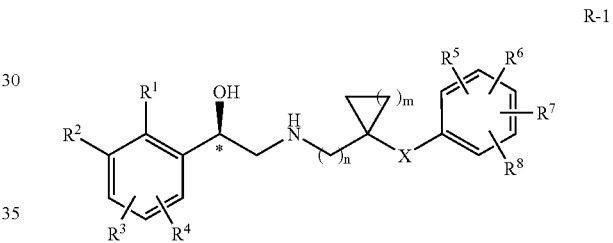

wherein the groups $R^1$, $R^2$, $R^3$, $R^4$, $R^5$, $R^6$, $R^7$, $R^8$, n, m and X may have the meanings given above.

By acid addition salts with pharmacologically acceptable acids are meant for example salts selected from the group comprising the hydrochloride, hydrobromide, hydroiodide, hydrosulphate, hydrophosphate, hydromethanesulphonate, hydronitrate, hydromaleate, hydroacetate, hydrobenzoate, hydrocitrate, hydroffumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Halogen within the scope of the present invention denotes fluorine, chlorine, bromine or iodine. Unless stated otherwise, fluorine and chlorine are the preferred halogens, while fluorine is generally preferred.

Unless otherwise stated, the alkyl groups (alkyl) are straight-chained or branched alkyl groups having 1 to 6, preferably 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated, the alkylene groups (alkylene) are branched and unbranched alkylene groups with 1 to 6, preferably 1 to 4 carbon atoms. The following are mentioned by way of example: methylene, ethylene, propylene or butylene. Unless otherwise stated, the definitions propylene and butylene include all the possible isomeric forms of the groups in question.

Unless otherwise stated, the alkenylene groups (alkenylene) are branched and unbranched alkenylene groups with 1 to 6, preferably 1 to 4 carbon atoms. The following are mentioned by way of example: ethenylene, propenylene or butenylene.

Unless otherwise stated, the cycloalkyl groups (cycloalkyl) are cyclic alkyl groups with 3 to 6. The following are mentioned by way of example: cyclopropyl, cyclobutanyl, cyclopentyl or cyclohexyl. Hydroxyalkyl groups within the scope of the present invention are cycloalkyl groups wherein one or more, preferably one hydrogen atom is substituted by hydroxy.

Unless otherwise stated, the alkyloxy groups (O-alkyl) are branched and unbranched alkyl groups with 1 to 6, preferably 1 to 4 carbon atoms which are linked via an oxygen atom. The following are mentioned by way of example: methyloxy, ethyloxy, propyloxy or butyloxy. In some cases the abbreviations —OMe, —OEt, —OProp or —OBu may be used to denote the methyloxy, ethyloxy, propyloxy or butyloxy groups. Unless otherwise stated, the definitions propyloxy and butyloxy include all the possible isomeric forms of the groups in question. Thus, for example, propyloxy includes n-propyloxy and iso-propyloxy, butyloxy includes iso-butyloxy, sec.butyloxy and tert.-butyloxy, etc. In some cases the term alkoxy may be used instead of alkyloxy within the scope of the present invention. The groups methyloxy, ethyloxy, propyloxy or butyloxy may therefore also be referred to by the names methoxy, ethoxy, propoxy or butoxy.

Unless otherwise stated, the haloalkylene groups (haloalkyl) are branched and unbranched alkyl groups with 1 to 6 carbon atoms, wherein one or more hydrogen atoms are replaced by halogen atoms, preferably by fluorine. Examples include: $CHF_2$, $CF_3$, $CH_2CF_3$, $CF_2CF_3$.

Unless otherwise stated, the aryl groups are aromatic ring systems with 6 to 10 carbon atoms. Preferred aryl groups are phenyl and naphthyl, while phenyl is particularly preferred according to the invention.

Unless otherwise stated, the heterocyclic groups (heterocycles) are aromatic or non-aromatic ring systems with 2 to 5 carbon atoms and 1, 2 or 3 atoms selected from the group O, S or N, preferably N. Particularly preferred heterocycles are piperidine, piperazine, morpholine, pyrolidine, pyrrole, imidazole, triazole, pyridine, pyrimidine, thiophene, tetrahydrofuran or furan.

The compounds according to the invention may be prepared analogously to methods already known in the art. Suitable methods of preparation are known for example from WO95/33724, which is hereby incorporated in its entirety by reference.

Essential components for preparing the compounds of general formula 1 according to the invention are particularly the cycloalkylamines of formula 2,

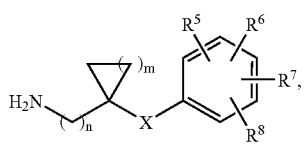

2 wherein the groups $R^5$, $R^6$, $R^7$, $R^8$, n, m and X may have the meanings given above.

The compounds of formula 2 may be prepared analogously to methods known in the art (Bertus et al., J. Org. Chem. 2002, 67, 3965-3968).

The compounds of formula 2 are not known in the art. Accordingly, in another aspect, the present invention relates to the compounds of formula 2, wherein
n denotes 0 or 1;
m denotes 1;
X denotes a single bond or one of the double-bonded groups —O, —NH, —S, $C_2$-$C_6$-alkenylene, —O—$C_1$-$C_6$-alkylene, —NH—$C_1$-$C_6$-alkylene, —S—$C_1$-$C_6$-alkylene or $C_1$-$C_6$-alkylene;
$R^5$, $R^6$, $R^7$ and $R^8$, which may be identical or different, denote hydrogen, $OR^9$, —$C_1$-$C_6$-alkyl, —$C_1$-$C_6$-haloalkyl, —$C_{1-C6}$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$ or halogen, or
two of the groups $R^5$, $R^6$, $R^7$ and $R^8$, if they are located vicinally to the substituting phenyl ring, together form a double-bonded group selected from $C_2$-$C_6$-alkylene, $C_2$-$C_6$-alkenylene and —O—$C_1$-$C_6$-alkylene-O— wherein in each case one or 2 hydrogen atoms may be replaced by one or two groups selected from among —$C_1$-$C_4$-alkyl, —$C_1$-$C_4$-alkoxy, OH, or halogen;
$R^9$ denotes hydrogen, $C_1$-$C_4$-alkyl, $C_6$-$C_{10}$-aryl or $C_6$-$C_{10}$-aryl-$C_1$-$C_4$-alkylene;
$R^{10}$ and $R^{11}$ which may be identical or different, denote hydrogen, $C_1$-$C_4$-alkyl, $C_6$-$C_{10}$-aryl or $C_6$-$C_{10}$-aryl-$C_1$-$C_4$-alkylene;
$R^{12}$ $C_1$-$C_4$-alkyl, $C_6$-$C_{10}$-aryl or $C_6$-$C_{10}$-aryl-$C_1$-$C_4$-alkylene;

optionally in the form of the individual optical isomers, mixtures of the individual enantiomers or racemates.

Preferred are compounds of general formula 2, wherein
n denotes 0 or 1, preferably 0;
m denotes 1;
X denotes a single bond or one of the double-bonded groups $C_2$-$C_4$-alkenylene, —O—$C_1$-$C_4$-alkylene, —NH—$C_1$-$C_4$-alkylene, —S—$C_1$-$C_4$-alkylene or $C_1$-$C_4$-alkylene;
$R^5$, $R^6$, $R^7$ and $R^8$, which may be identical or different, denote hydrogen, $OR^9$, —$C_1$-$C_4$-alkyl, —$C_1$-$C_4$-haloalkyl, —$C_1$-$C_4$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$, fluorine, chlorine or bromine, or
two of the groups $R^5$, $R^6$, $R^7$ and $R^8$, if they are located vicinally to the substituting phenyl ring, together form a double-bonded group selected from $C_2$-$C_4$-alkylene, $C_2$-$C_4$-alkenylene and —O—$C_1$-$C_4$-alkylene-O— wherein in each case one or 2 hydrogen atoms may be replaced by one or two groups selected from among methyl, methoxy, OH, fluorine, chlorine or bromine;
$R^9$ denotes hydrogen, methyl, ethyl, phenyl, naphthyl, benzyl, naphthylmethyl or 2-phenylethyl;
$R^{10}$ and $R^{11}$ which may be identical or different, denote hydrogen, methyl, ethyl, phenyl, naphthyl, naphthylmethyl, benzyl or 2-phenylethyl;

$R^{12}$ denotes methyl, ethyl, phenyl, naphthyl, naphthylmethyl, benzyl or 2-phenylethyl;

optionally in the form of the individual optical isomers, mixtures of the individual enantiomers or racemates.

Particularly preferred are compounds of general formula 2, wherein n denotes 0 or 1, preferably 1;

m denotes 1;

X denotes a single bond or one of the double-bonded groups —$CH_2$—, —$CH_2$—$CH_2$—, —$CH_2$—$CH_2$—$CH_2$—, —CH=CH—, —$CH_2$—CH=CH—, —$CH_2$—O—, —$CH_2$—$CH_2$—O—, —$CH_2$—O—, —$CH_2$—$CH_2$—O—, —$CH_2$—$NH_2$—, —$CH_2$—$CH_2$—$NH_2$—;

$R^5, R^6, R^7$ and $R^8$, which may be identical or different, denote hydrogen, OH, methyl, ethyl, propyl, butyl, —$CH_2F$, —$CHF_2$, —$CF_3$, —$CH_2$—$CH_2F$, —$CH_2$—$CHF_2$, —$CH_2$—$CF_3$, —$CH_2$—$CH_2$—OH, —$CH_2$—OH, cyclopropyl, cyclobutyl, cyclopentyl, HO-cyclopropyl, HO-cyclobutyl, HO-cyclopentyl, —CN, $NO_2$, —COphenyl, —COOmethyl, —COOethyl, —$CONH_2$, —CONHmethyl, —CONHphenyl, —CONHbenzyl, —CON(methyl)$_2$, $NH_2$, NH(methyl), N(methyl)$_2$, —NHCOmethyl, —NHCOphenyl, —$NHSO_2$methyl, —$NHSO_2$phenyl, —$NHSO_2$-phenyl-$CH_3$, —$SO_2$methyl, —$SO_2$-phenyl, —$SO_2$-phenyl-$CH_3$, —$SO_2NH_2$, fluorine, chlorine or bromine, or two of the groups $R^5, R^6, R^7$ and $R^8$, if they are located vicinally to the substituting phenyl ring, together form a double-bonded group selected from —$CH_2$—$CH_2$—$CH_2$—, —$CH_2$—$CH_2$—$CH_2$—$CH_2$—, —$CH_2$—CH=CH—, —CH=CH—CH=CH—, —O—$CH_2$—O— and —O—$CH_2$—$CH_2$—O— wherein in each case one or 2 hydrogen atoms may be replaced by one or two groups selected from among methyl, methoxy, OH or fluorine, optionally in the form of the individual optical isomers, mixtures of the individual enantiomers or racemates.

Particularly preferred are compounds of formula 2, wherein

X denotes a single bond or one of the double-bonded groups —$CH_2$—, —$CH_2CH_2$—, —$CH_2$—O, preferably a single bond or one of the double-bonded groups —O—$CH_2$— and —$CH_2$—, particularly preferably —$CH_2$—, and wherein the groups $R^5, R^6, R^7, R^8$, n and m may have the meanings given hereinbefore, optionally in the form of the individual optical isomers, mixtures of the individual enantiomers or racemates.

Also particularly preferred are compounds of formula 2, wherein $R^5, R^6, R^7$ and $R^8$, which may be identical or different, denote hydrogen, OH, methyl, ethyl, propyl, butyl, $CHF_2$, $CH_2F$, $CF_3$, —$CH_2$—$CH_2$—OH, —$CH_2$—OH, methyloxy, ethyloxy, propyloxy, butyloxy, cyclopropyl, hydroxycyclopropyl, $NH_2$, NHmethyl, N(methyl)$_2$, fluorine, chlorine or bromine, or two of the groups $R^5, R^6, R^7$ and $R^8$, if they are located vicinally to the substituting phenyl ring, denote the double-bonded group —CH=CH—CH=CH— wherein in each case one or 2 hydrogen atoms may be replaced by one or two groups selected from among methyl, methoxy, OH, fluorine, chlorine or bromine, and wherein the groups n, m and X may have the meanings given hereinbefore, optionally in the form of the individual optical isomers, mixtures of the individual enantiomers or racemates.

Also particularly preferred are compounds of formula 2, wherein $R^5, R^6, R^7$ and $R^8$, which may be identical or different, denote hydrogen, OH, methyl, ethyl, propyl, butyl, $CHF_2$, $CH_2F$, $CF_3$, methyloxy, ethyloxy, propyloxy, butyloxy, cyclopropyl, hydroxycyclopropyl, $NH_2$, fluorine, chlorine or bromine, and wherein the groups n, m and X may have the meanings given hereinbefore, optionally in the form of the individual optical isomers, mixtures of the individual enantiomers or racemates.

Also particularly preferred are compounds of formula 2, wherein $R^5, R^6, R^7$ and $R^8$, which may be identical or different, denote hydrogen, OH, methyl, $CF_3$, methyloxy, ethyloxy, propyloxy, butyloxy, hydroxycyclopropyl, $NH_2$, fluorine or chlorine, and wherein the groups n, m and X may have the meanings given above, optionally in the form of the individual optical isomers, mixtures of the individual enantiomers or racemates.

Also particularly preferred are compounds of formula 2, wherein $R^5$ and $R^8$ denotes hydrogen;

$R^6$ and $R^7$, if they are located vicinally to the substituting phenyl ring, together denote the double-bonded group —CH=CH—CH=CH—, and wherein the groups n, m and X may have the meanings given hereinbefore, optionally in the form of the individual optical isomers, mixtures of the individual enantiomers or racemates.

In a preferred aspect the present invention also relates to compounds of general formula 2, wherein n denotes 0 or 1, preferably 0;

m denotes 1;

X denotes a single bond or one of the double-bonded groups —$CH_2$—, —$CH_2$—$CH_2$—, —$CH_2$—$CH_2$—$CH_2$—, —CH=CH—, —$CH_2$—CH=CH—, —$CH_2$—O—, —$CH_2$—$CH_2$—O—, —$CH_2$—$NH_2$—, —$CH_2$—$CH_2$—$NH_2$—;

$R^5$ and $R^8$ which may be identical or different, denote hydrogen, methyl, methyloxy or fluorine;

$R^6$ and $R^7$ which may be identical or different, denote hydrogen, OH, methyl, ethyl, $CF_3$, methyloxy, ethyloxy, propyloxy, butyloxy, cyclopropyl, hydroxycyclopropyl, $NH_2$ or fluorine, or $R^6$ and $R^7$, if they are located vicinally to the substituting phenyl ring, together form the double-bonded group —CH=CH—CH=CH— wherein in each case one or 2 hydrogen atoms may be replaced by one or two groups selected from among methyl, methoxy, OH, fluorine, chlorine and bromine, optionally in the form of the individual optical isomers, mixtures of the individual enantiomers or racemates.

Preferred are compounds of general formula 2, wherein n denotes 0 or 1, preferably 0;

m denotes 1;

X denotes a single bond or one of the double-bonded groups —$CH_2$—, —$CH_2CH_2$—, —$CH_2$—O, preferably a single bond or one of the double-bonded groups —O—$CH_2$— and —$CH_2$—, particularly preferably —$CH_2$—, $R^5$ and $R^8$ which may be identical or different, denote hydrogen, methyl, methyloxy or fluorine;

$R^6$ and $R^7$ which may be identical or different, denote hydrogen, OH, methyl, $CF_3$, methyloxy, ethyloxy, propyloxy, butyloxy, hydroxycyclopropyl, $NH_2$ or fluorine, or $R^6$ and $R^7$, if they are located vicinally to the substituting phenyl ring, together form the double-bonded group —CH=CH—CH=CH, optionally in the form of the individual optical isomers, mixtures of the individual enantiomers or racemates.

Particularly preferred are compounds of general formula 2, wherein $R^5$, $R^6$ and $R^8$ which may be identical or different, denote hydrogen or methyl, preferably hydrogen;

$R^7$ denotes hydrogen, OH, methyl, $CF_3$, methyloxy, ethyloxy, propyloxy or butyloxy, preferably OH, methyloxy, ethyloxy, propyloxy or butyloxy, and n, m and X may have the meanings given above, optionally in the form of the individual optical isomers, mixtures of the individual enantiomers or racemates.

Particularly preferred compounds of formula 2 are selected from among:

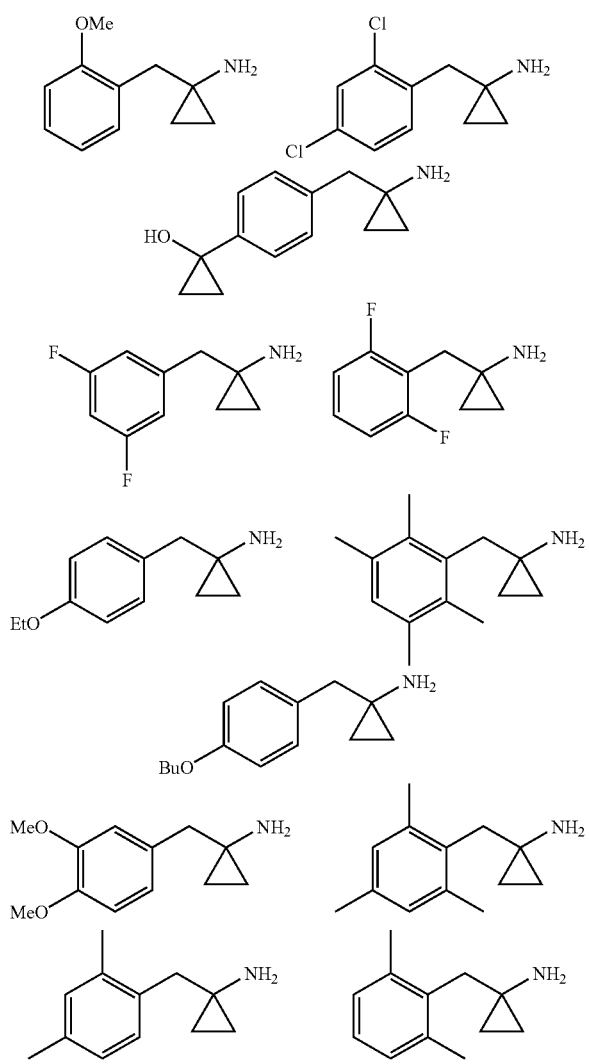

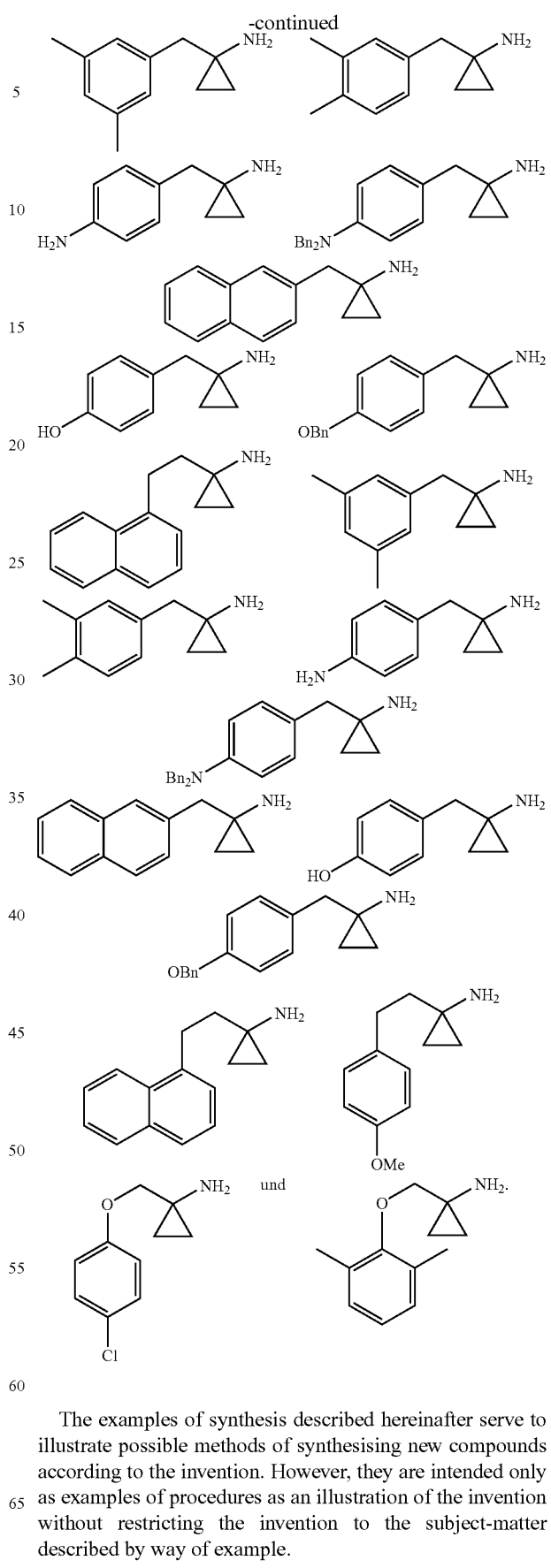

The examples of synthesis described hereinafter serve to illustrate possible methods of synthesising new compounds according to the invention. However, they are intended only as examples of procedures as an illustration of the invention without restricting the invention to the subject-matter described by way of example.

Synthesis of the Intermediates:

General Method 1:

1 equivalent titanium tetraisopropoxide is added dropwise at −15 to −25° C. to a solution of 1 equivalent (typically approximately 30 mmol) of phenylacetonitrile in 150 mL diethyl ether. The mixture is stirred for 30 minutes at ambient temperature and then combined with 2 equivalents of boron trifluoride diethyl etherate, while the reaction mixture is cooled such that the temperature does not exceed 20° C. The mixture is stirred for 30 minutes, 120 mL of 1 M sodium hydroxide solution are slowly added dropwise and the mixture is stirred for a further 60 minutes. The aqueous phase is separated off and extracted with diethyl ether. Then the combined ether phases are washed with sodium sulphite solution and extracted with 0.5 molar hydrochloric acid. The hydrochloric acid fraction containing the product is made alkaline with sodium hydroxide solution and extracted with dichloromethane. The organic phases are dried with sodium sulphate and evaporated down. The residue is purified by chromatography on a silica gel column (dichloromethane/methanol/ammonia gradient).

1-(2,3,5,6-tetramethyl-benzyl)-cyclopropylamine

Prepared from 5.0 g (29 mmol) (2,3,5,6-tetramethyl-phenyl)-acetonitrile according to general method 1.
Yield: 2.5 g (43%); mass spectroscopy: $[M+H]^+$=204.

1-(3,4-dimethoxy-benzyl)-cyclopropylamine

The compound is prepared according to general method 1 from 5.2 g (29 mmol) (3,4-dimethoxy-phenyl)-acetonitrile.
Yield: 1.6 g (27%); mass spectroscopy: $[M+H]^+$=208.

1-(4-butoxy-benzyl)-cyclopropylamine

Prepared according to general method 1 from 5.6 g (29 mmol) (4-butoxy-phenyl)-acetonitrile.
Yield: 2.7 g (43%); mass spectroscopy: $[M+H]^+$=220.

1-(4-ethoxy-benzyl)-cyclopropylamine

Prepared according to general method 1 from 4.7 g (29 mmol) (4-ethoxy-phenyl)-acetonitrile.
Yield: 1.9 g (35%); mass spectroscopy: $[M+H]^+$=192.

1-(2,6-difluoro-benzyl)-cycloprolpylamine

Prepared analogously to general method 1 from 5.0 g (33 mmol) (2,6-difluoro-phenyl)-acetonitrile. Yield: 3.0 g (50%); mass spectroscopy: $[M+H]^+$=184.

1-(4-chloro-benzyl)-cyclopropylamine

Prepared according to general method 1 from 4.5 g (29 mmol) (4-chloro-phenyl)-acetonitrile.
Yield: 2.0 g (38%); mass spectroscopy: $[M+H]^+$=182/4.

1-[4-(1-amino-cyclopropylmethyl)-phenyl]-cyclopropanol 4.0 g (21 mmol) ethyl 4-cyanomethyl-benzoate are reacted and worked up analogously to general method 1. Yield: 0.6 g (14%); mass spectroscopy: $[M+H]^+$=204.

1-(3,5-difluoro-benzyl)-cyclopropylamine

Prepared according to general method 1 from 5.0 g (32 mmol) (3,5-difluoro-phenyl)-acetonitrile. Yield: 2.7 g (47%); mass spectroscopy: $[M+H]^+$=184.

1-(4-trifluoromethyl-benzyl)-cyclopropylamine

The compound is prepared according to general method 1 from 5.0 g (26 mmol) (4-trifluoromethyl-phenyl)-acetonitrile. Yield: 3.1 g (54%); mass spectroscopy: $[M+H]^+$=216.

1-(2,4-dichloro-benzyl)-cyclopropylamine

Prepared according to general method 1 from 6.3 g (33 mmol) (2,4-dichloro-phenyl)-acetonitrile. Yield: 3.1 g (43%); mass spectroscopy: $[M+H]^+$=216/218/220.

1-(2-chloro-benzyl)-cyclopropylamine

Prepared according to general method 1 from 5.1 g (34 mmol) (2-chloro-phenyl)-acetonitrile.
Yield: 2.3 g (38%); mass spectroscopy: $[M+H]^+$=182/184.

1-(4-trifluoromethoxy-benzyl)-cyclopropylamine

Prepared according to general method 1 from 5.0 g (25 mmol) (4-trifluoromethoxy-phenyl)-acetonitrile. Yield: 2.9 g (51%); mass spectroscopy: $[M+H]^+$=232.

1-(2-methoxy-benzyl)-cyclopropylamine

Prepared according to general method 1 from 5.0 g (34 mmol) (2-methoxy-phenyl)-acetonitrile. Yield: 1.7 g (28%); mass spectroscopy: $[M+H]^+$=178.

1-(2,6-dimethyl-benzyl)-cyclopropylamine

The compound is prepared according to general method 1 from 5.8 g (40 mmol) (2,6-dimethyl-phenyl)-acetonitrile.
Yield: 1.4 g (20%); mass spectroscopy: $[M+H]^+$=176.

1-(2,4,6-trimethyl-benzyl)-cyclopropylamine

Prepared according to general method 1 from 5.0 g (31 mmol) (2,4,6-trimethyl-phenyl)-acetonitrile. Yield: 2.2 g (37%); mass spectroscopy: $[M+H]^+$=190.

1-(2,4-dimethyl-benzyl)-cyclopropylamine

Prepared according to general method 1 from 5.0 g (34 mmol) (2,4-dimethyl-phenyl)-acetonitrile. Yield: 1.9 g (32%); mass spectroscopy: $[M+H]^+$=176.

1-(2,6-dichloro-benzyl)-cyclopropylamine

Prepared according to general method 1 from 5.2 g (27 mmol) (2,6-dichloro-phenyl)-acetonitrile. Yield: 2.7 g (46%); mass spectroscopy: $[M+H]^+$=216/218/220.

1-(2-trifluoromethyl-benzyl)-cyclopropylamine

The amine is according to general method 1 from 5.0 g (27 mmol) (2-trifluoromethyl-phenyl)-acetonitrile prepared. Yield: 2.8 g (48%); mass spectroscopy: $[M+H]^+$=216.

1-(3-methyl-benzyl)-cycloproplylamine

Prepared according to general method 1 from 5.4 g (40 mmol) m-tolyl-acetonitrile. Yield: 1.7 g (26%); mass spectroscopy: $[M+H]^+=162$.

1-(2-methyl-benzyl)-cyclopropylamine

Prepared according to general method 1 from 3.5 mL (28 mmol) o-tolyl-acetonitrile. Yield: 0.58 g (13%); mass spectroscopy: $[M+H]^+=162$.

1-(3,5-dimethyl-benzyl)-cyclopropylamine

Prepared according to general method 1 from 5.9 g (40 mmol) (3,5-dimethyl-phenyl)-acetonitrile. Yield: 3.8 g (54%); mass spectroscopy: $[M+H]^+=176$.

1-(3,4-dimethyl-benzyl)-cyclopropylamine

The amine is obtained according to general method 1 from 5.9 g (40 mmol) (3,4-dimethyl-methyl-phenyl)-acetonitrile. Yield: 2.4 g (34%); mass spectroscopy: $[M+H]^+=176$.

1-benzyl-cyclopropylamine

Prepared according to general method 1 from 4.7 g (40 mmol) phenyl-acetonitrile. Yield: 2.3 g (39%); mass spectroscopy: $[M+H]^+=148$.

1-(4-methoxy-benzyl)-cyclopropylamine

The amine is obtained according to general method 1 from 5.5 mL (40 mmol) (4-methoxy-phenyl)-acetonitrile. Yield: 4.2 g (59%); mass spectroscopy: $[M+H]^+=178$.

1-phenoxymethyl-cyclopropylamine

The amine is obtained according to general method 1 from 3.94 g (29 mmol) phenoxy-acetonitrile. Yield: 1.80 g (38%); mass spectroscopy: $[M+H]^+=164$.

1-(2,6-dimethyl-phenoxymethyl)-cyclopropylamine

The amine is obtained according to general method 1 from 4.80 g (30 mmol) (2,6-dimethyl-phenoxy)-acetonitrile. Yield: 2.56 g (45%); mass spectroscopy: $[M+H]^+=192$.

1-[2-(4-methoxy-phenyl)-ethyl]-cyclopropylamine

Prepared according to general method 1 from 5.00 g (31 mmol) 3-(4-methoxy-phenyl)-propionitrile. Yield: 1.90 g (32%); mass spectroscopy: $[M+H]^+=192$.

1-naphthalen-2-ylmethyl-cyclopropylamine

The amine is prepared according to general method 1 from 5.75 g (33 mmol) naphthalen-2-yl-acetonitrile. Yield: 2.30 g (35%); mass spectroscopy: $[M+H]^+=198$.

1-(4-benzyloxy-benzyl)-cyclopropylamine

The compound is prepared analogously to general method 1 from 25 g (112 mmol) naphthalen-2-yl-acetonitrile. Yield: 14.1 g (50%); mass spectroscopy: $[M+H]^+=254$.

4-(1-amino-cyclopropylmethyl)-phenol

Hydrogenation of 5.00 g (19.7 mmol) 1-(4-benzyloxy-benzyl)-cyclopropylamine in 60 mL methanol at 3 bar with palladium on charcoal as catalyst. Yield: 2.25 g (70%); mass spectroscopy: $[M+H]^+=164$.

1-(2-naphthalen-1-yl-ethyl)-cyclopropylamine

The amine is prepared according to general method 1 from 5.4 g (30 mmol) 3-naphthalen-1-yl-propionitrile. Yield: 2.2 g (35%); mass spectroscopy: $[M+H]^+=212$.

1-(4-chloro-phenoxymethyl)-cyclopropylamine

The amine is prepared according to general method 1 from 4.86 g (29 mmol) (4-chloro-phenoxy)-acetonitrile. Yield: 2.7 g (47%); mass spectroscopy: $[M+H]^+=198/200$.

[4-(1-amino-cyclopropylmethyl)-phenyl]-dibenzyl-amine

Reaction of 32 g (102 mmol) (4-dibenzylamino-phenyl)-acetonitrile according to general method 1. Yield: 14.1 g (40%); mass spectroscopy: $[M+H]^+=343$.

4-(1-amino-cyclopropylmethyl)-phenylamine 3.0 g (8.8 mmol) [4-(1-amino-cyclopropylmethyl)-phenyl]-dibenzyl-amine are dissolved in 30 mL methanol and hydrogenated at 3 bar in the presence of palladium on charcoal. Then the catalyst is filtered off and the filtrate is evaporated down. The residue is dissolved in diethyl ether and combined with 4 molar hydrochloric acid in dioxane. After the solvent has been distilled off the hydrochloride is suspended in diisopropylether for further purification.

Yield: 1.5 g (86%; hydrochloride); mass spectroscopy: $[M+H]^+=163/65$.

General Method 2 (Synthesis of cyclopentyl- and cyclohexylamines)

A solution of 1 equivalent (usually 70 mmol) ketone in 70 mL THF is added dropwise at −20° C. to 1.1 equivalents Grignard reagent in THF. After 30 minutes stirring at ambient temperature the reaction is stopped by the addition of ammonium chloride solution and the mixture is extracted with dichloromethane. The organic phases are dried with sodium sulphate and freed from solvent. The residue is further reacted directly without any further purification.

For this the alcohol and 8.7 mL (69.5 mmol) trimethylsilylcyanide are combined at 10° C. with 10.7 mL acetic acid. Then 14 mL conc. sulphuric acid is added dropwise so that the temperature does not exceed 20° C. After two hours' stirring at ambient temperature 140 mL 6 molar sodium hydroxide solution and 100 mL tert-butylether are added. The organic phase is separated off, dried with sodium sulphate and evaporated down. The formamide present as an oil is dissolved in 16 mL ethanol, combined with 50 mL of a 20 molar sodium hydroxide solution and refluxed overnight. After cooling to ambient temperature and adding toluene the phases are separated. The organic phase is washed with water, dried with sodium sulphate and freed from the solvent. The residue is dissolved in ethyl acetate and combined with 10% hydrochloric acid in ethyl acetate until an acid reaction takes place. The precipitated hydrochloride is filtered off and dried.

1-phenethyl-cyclohexylamine

Prepared from 2.0 g (20.4 mmol) cyclohexanone and phenethylmagnesium chloride (1 molar solution in tetrahydrofuran) according to general method 2. Yield: 1.44 g (29%; hydrochloride). Mass spectroscopy: $[M+H]^+=204$.

1-benzyl-cyclopentylamine

Prepared from 2.3 g (27.3 mmol) cyclopentanone and benzylmagnesium chloride (2 molar solution in tetrahydrofuran) according to general method 2.

Yield: 1.56 g (27%; hydrochloride). Mass spectroscopy: $[M+H]^+=176$.

1-(4-Fluorobenzyl)-cyclopentylamine

Prepared from 2.7 g (32.1 mmol) cyclopentanone and 4-fluorobenzylmagnesium chloride (0.25 molar solution in tetrahydrofuran) according to general method 2.

Yield: 3.72 g (50%; hydrochloride). Mass spectroscopy: $[M+H]^+=194$.

1-[2-(4-methoxyphenyl)-ethyl]-cyclohexylamine

Prepared from 4.0 g (40.7 mmol) cyclohexanone and 4-methoxyphenethylmagnesium chloride (2 molar solution in tetrahydrofuran) according to general method 2.

Yield: 2.53 g (23%; hydrochloride). Mass spectroscopy: $[M+H]^+=234$.

1-(4-methoxy-benzyl)-cyclopentylamine 4-(1-amino-cyclopentylmethyl)-phenylamine A solution of 2.1 g (8.4 mmol) 1-nitro-4-(1-nitrocyclopentylmethyl)-benzene (prepared according to the prescribed method of Hass et. al., *J. Org. Chem.* 1949, 71, 2290-2291) in 60 mL methanol is hydrogenated with Raney Nickel as catalyst at 3 bar. Then the catalyst is filtered off and the filtrate freed from the solvent. The residue is dissolved in 15 mL ethanol and combined with 10% hydrochloric acid in ethanol until an acid reaction takes place. After removal of the solvents by distillation the residue is suspended in 20 mL ethanol and filtered.

Yield: 1.4 g (hydrochloride).

1-(4-methoxy-benzyl)-cyclopentylamine 1.4 g (6.17 mmol) 4-(1-aminocyclopentylmethyl)-phenylamine hydrochloride are placed in 25 mL methanol and at 0° C. combined with 2.24 mL (27 mmol) conc. hydrochloric acid. At this temperature 0.51 g (7.41 mmol) sodium nitrite in 1 mL water are added dropwise within 30 minutes. After 2 hours stirring the reaction mixture is allowed to come up to ambient temperature and then refluxed for 3 hours. The solvents are distilled off and the residue is combined with ethyl acetate. It is washed with aqueous ammonia solution, dried with sodium sulphate and evaporated down. The residue is dissolved in ethanol and combined with 10% hydrochloric acid in ethanol. The product precipitated as a salt is filtered off, washed with ethanol and dried. Yield: 0.56 g (27% over 2 steps, hydrochloride), mass spectroscopy: $[M+H]^+=206$.

1-(4-methoxy-benzyl)-cyclohexylamine

Obtained from 4.7 g (17.8 mmol) of 1-nitro-4-(1-nitrocyclohexylmethyl)-benzene (prepared according to the prescribed method of H. B. Hass et al., J. Org. Chem. 1949, 71, 2290-2291) analogously to the method described hereinbefore. Yield: 3.85 g (84%, hydrochloride). Mass spectroscopy: $[M+H]^+=220$.

1-[2-(4-fluoro-phenyl)-ethyl]-cyclohexylamine 2.5 g (11.3 mmol) 1-fluoro-4-iodo-benzene, 1.5 g (11.9 mmol) 1-ethynyl-cyclohexylamine, 793 mg (1.13 mmol) $PdCl_2(PPh_3)_2$, 67 mg (0.35 mmol) copper iodide and 50 mL diisopropylamine are stirred for 2 hours at 70° C. Then the base is distilled off and the residue is combined with ethyl acetate. The insoluble constituents are filtered off and the filtrate is evaporated down. The alkyne thus prepared is dissolved in 35 mL THF and 35 mL toluene and hydrogenated with platinum oxide as catalyst at normal pressure. The catalyst is separated off and the filtrate is freed from the solvent. The crude product is dissolved in ethyl acetate and combined with 10% hydrochloric acid in ethyl acetate. The precipitated solid is filtered off and washed with ethyl acetate. Yield: 1.3 g (45%; hydrochloride); mass spectroscopy: $[M+H]^+=222$.

Synthesis of the Compounds of General Formula 1:

General Method 3:

1 mmol glyoxalaldehyde or -acetal and 1 mmol amine are stirred for 30 minutes in 5 mL tetrahydrofuran at ambient temperature. The mixture is cooled to 0° C. and under an argon atmosphere 1.5 mL of a 2 molar solution of lithium borohydride in tetrahydrofuran is added dropwise thereto. The mixture is stirred for 30 min at ambient temperature, combined with 10 mL dichloromethane and 3 mL water, stirred for a further hour and then filtered through kieselguhr, while eluting with dichloromethane. The eluate is freed from the solvent and the residue is purified by chromatography, if necessary. The benzylether thus obtained is dissolved in methanol and hydrogenated with palladium on charcoal (10%) as catalyst at 2.5 bar and ambient temperature. Then the catalyst is separated off and the crude product is purified by chromatography (reverse phase, acetonitrile/water gradient with 0.1% trifluoroacetic acid) or recrystallised from acetonitrile.

General Method 4 (debenzylation with boron tribromide)

1 mmol glyoxalaldehyde or -acetal and 1 mmol amine are first of all reacted and worked up as described in General Method 3. Then the benzylether obtained is dissolved in 3 mL dichloromethane and cooled to −78° C. At this temperature 2 mL of a 1 molar boron tribromide solution in dichloromethane is slowly added dropwise. The reaction mixture is brought to ambient temperature, stirred for a further 10 minutes and then diluted with 3 mL water and 10 mL dichloromethane. The solution is added to a short column filled with kieselguhr and washed again with dichloromethane and methanol. The eluate is evaporated down and the residue is chromatographed (reverse phase, acetonitrile/water gradient with 0.1% trifluoroacetic acid).

EXAMPLE 1

5-hydroxy-8-{1-hydroxy-2-[1-(4-methoxy-benzyl)-cyclopropylamino]-ethyl}-4H-benzo[1,4]oxazin-3-one

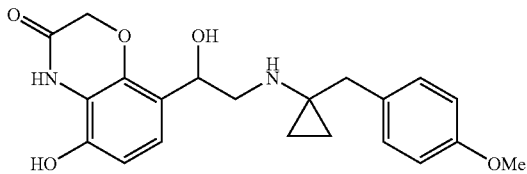

Reaction of 329 mg (1 mmol) 5-benzyloxy-8-(2,2-dihydroxy-acetyl)-4H-benzo[1,4]oxazin-3-one and 177 mg (1 mmol) 1-(4-methoxy-benzyl)-cyclopropylamine according to general method 3. Yield: 39 mg (8%, trifluoroacetate); mass spectroscopy: [M+H]$^+$=385.

EXAMPLE 2

8-[2-(1-benzyl-cyclopropylamino)-1-hydroxy-ethyl]-5-hydroxy-4H-benzo[1,4]oxazin-3-one

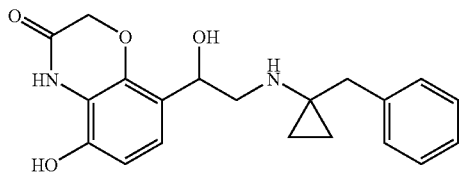

Prepared according to general method 3 from 329 mg (1 mmol) 5-benzyloxy-8-(2,2-dihydroxy-acetyl)-4H-benzo[1,4]oxazin-3-one and 147 mg (1 mmol) 1-benzyl-cyclopropylamine. Yield: 56 mg (12%, trifluoroacetate); mass spectroscopy: [M+H]$^+$=355.

EXAMPLE 3

8-{2-[1-(2,6-dimethyl-benzyl)-cyclopropylamino]-1-hydroxy-ethyl}-5-hydroxy-4H-benzo[1,4]oxazin-3-one

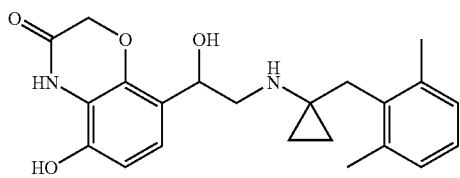

The compound is prepared according to general method 3 from 329 mg (1 mmol) 5-benzyloxy-8-(2,2-dihydroxy-acetyl)-4H-benzo[1,4]oxazin-3-one and 175 mg (1 mmol) 1-(2,6-dimethyl-benzyl)-cyclopropylamine. Yield: 52 mg (11%, trifluoroacetate); mass spectroscopy: [M+H]$^+$=383.

EXAMPLE 4

8-{2-[1-(3,4-dimethyl-benzyl)-cyclopropylamino]-1-hydroxy-ethyl}-5-hydroxy-4H-benzo[1,4]oxazin-3-one

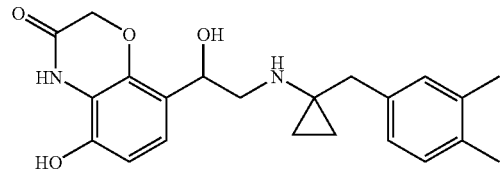

Prepared according to general method 3 from 329 mg (1 mmol) 5-benzyloxy-8-(2,2-dihydroxy-acetyl)-4H-benzo[1,4]oxazin-3-one and 175 mg (1 mmol) 1-(3,4-dimethyl-benzyl)-cyclopropylamine. Yield: 233 mg (47%, trifluoroacetate); mass spectroscopy: [M+H]$^+$=383.

EXAMPLE 5

5-hydroxy-8-{1-hydroxy-2-[1-(3-methyl-benzyl)-cyclopropylamino]-ethyl}-4H-benzo[1,4]oxazin-3-one

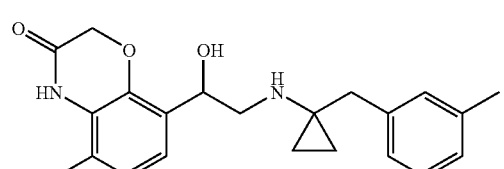

Prepared according to general method 3 from 329 mg (1 mmol) 5-benzyloxy-8-(2,2-dihydroxy-acetyl)-4H-benzo[1,4]oxazin-3-one and 161 mg (1 mmol) 1-(3-methyl-benzyl)-cyclopropylamine. Yield: 179 mg (37%, trifluoroacetate); mass spectroscopy: [M+H]$^+$=369.

EXAMPLE 6

5-hydroxy-8-{1-hydroxy-2-[1-(2-trifluoromethyl-benzyl)-cyclopronylamino]-ethyl}-4H-benzo[1,4]oxazin-3-one

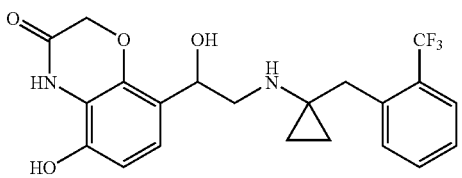

Prepared according to general method 3 from 329 mg (1 mmol) 5-benzyloxy-8-(2,2-dihydroxy-acetyl)-4H-benzo[1,4]oxazin-3-one and 215 mg (1 mmol) 1-(2-trifluoromethyl-benzyl)-cyclopropylamine. Yield: 13 mg (2%, trifluoroacetate); mass spectroscopy: [M+H]$^+$=423.

EXAMPLE 7

5-hydroxy-8-(1-hydroxy-2-{1-[4-(1-hydroxy-cyclopropyl)-benzyl]-cyclopropylamino}-ethyl)-4H-benzo1,4]oxazin-3-one

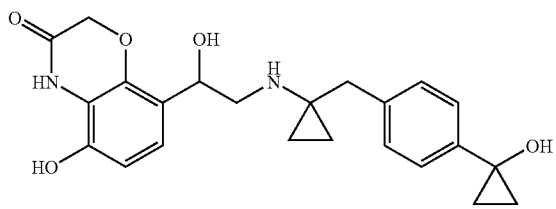

Prepared according to general method 3 from 329 mg (1 mmol) 5-benzyloxy-8-(2,2-dihydroxy-acetyl)-4H-benzo[1,4]oxazin-3-one and 203 mg (1 mmol) 1-[4-(1-amino-cyclopropylmethyl)-phenyl]-cyclopropanol. Yield: 29 mg (6%, trifluoroacetate); mass spectroscopy: $[M+H]^+=411$.

EXAMPLE 8

8-{2-[1-(3,5-difluoro-benzyl)-cyclopropylamino]-1-hydroxy-ethyl}-5-hydroxy-4H-benzo[1,4]oxazin-3-one

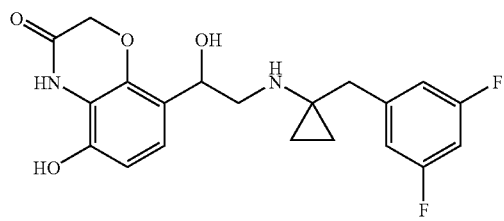

Prepared according to general method 3 from 329 mg (1 mmol) 5-benzyloxy-8-(2,2-dihydroxy-acetyl)-4H-benzo[1,4]oxazin-3-one and 183 mg (1 mmol) 1-(3,5-difluoro-benzyl)-cyclopropylamine. Yield: 66 mg (13%, trifluoroacetate); mass spectroscopy: $[M+H]^+=391$.

EXAMPLE 9

5-hydroxy-8-[1-hydroxy-2-(1-phenoxymethyl-cyclopropylamino)-ethyl]-4H-benzo[1,4]oxazin-3-one

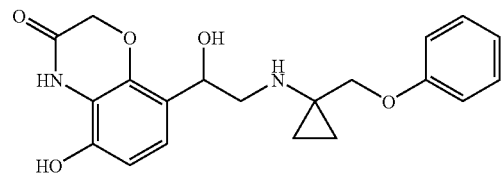

Prepared according to general method 3 from 329 mg (1 mmol) 5-benzyloxy-8-(2,2-dihydroxy-acetyl)-4H-benzo[1,4]oxazin-3-one and 163 mg (1 mmol) 1-phenoxymethyl-cyclopropylamine. Yield: 26 mg (5%, trifluoroacetate); mass spectroscopy: $[M+H]^+=371$.

EXAMPLE 10

5-hydroxy-8-{1-hydroxy-2-[1-(4-trifluoromethyl-benzyl)-cyclopropylamino]-ethyl}-4H-benzo[1,4]oxazin-3-one

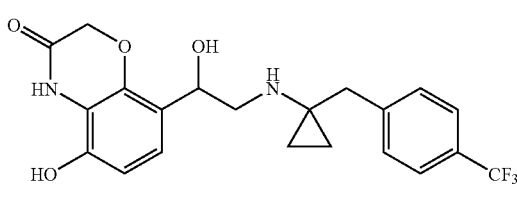

Prepared according to general method 3 from 329 mg (1 mmol) 5-benzyloxy-8-(2,2-dihydroxy-acetyl)-4H-benzo[1,4]oxazin-3-one and 215 mg (1 mmol) 1-(4-trifluoromethyl-benzyl)-cyclopropylamine. Yield: 18 mg (3%, trifluoroacetate); mass spectroscopy: $[M+H]^+=423$.

EXAMPLE 11

5-hydroxy-8-{1-hydroxy-2-[1-(2-methoxy-benzyl)-cyclopropylamino]-ethyl}-4H-benzo[1,4]oxazin-3-one

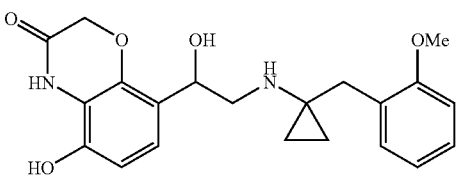

Prepared according to general method 3 from 329 mg (1 mmol) 5-benzyloxy-8-(2,2-dihydroxy-acetyl)-4H-benzo[1,4]oxazin-3-one and 177 mg (1 mmol) 1-(2-methoxy-benzyl)-cyclopropylamine. Yield: 100 mg (20%, trifluoroacetate); mass spectroscopy: $[M+H]^+=385$.

EXAMPLE 12

5-hydroxy-8-{1-hydroxy-2-[1-(2-methyl-benzyl)-cyclopropylamino]-ethyl}-4H-benzo[1,4]oxazin-3-one

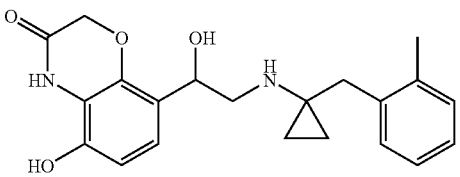

Prepared according to general method 3 from 329 mg (1 mmol) 5-benzyloxy-8-(2,2-dihydroxy-acetyl)-4H-benzo[1,4]oxazin-3-one and 161 mg (1 mmol) 1-(2-methyl-benzyl)-cyclopropylamine. Yield: 60 mg (16%, trifluoroacetate); mass spectroscopy: $[M+H]^+=369$.

EXAMPLE 13

8-{2-[1-(2,6-dimethyl-phenoxymethyl)-cyclopropylamino]-1-hydroxy-ethyl}-5-hydroxy-4H-benzo[1,4]oxazin-3-one

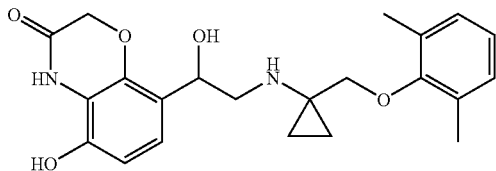

Prepared according to general method 3 from 329 mg (1 mmol) 5-benzyloxy-8-(2,2-dihydroxy-acetyl)-4H-benzo[1,4]oxazin-3-one and 191 mg (1 mmol) 1-(2,6-dimethyl-phenoxymethyl)-cyclopropylamine. Yield: 194 mg (49%, trifluoroacetate); mass spectroscopy: $[M+H]^+=399$.

EXAMPLE 14

5-hydroxy-8-[1-hydroxy-2-(1-naphthalen-2-ylmethyl-cyclopropylamino)-ethyl]-4H-benzo[1,4]oxazin-3-one

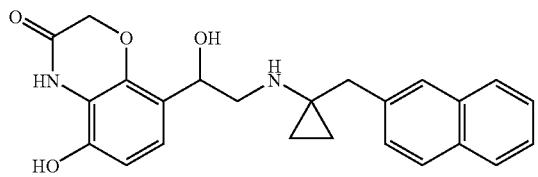

Prepared according to general method 3 from 329 mg (1 mmol) 5-benzyloxy-8-(2,2-dihydroxy-acetyl)-4H-benzo[1,4]oxazin-3-one and 197 mg (1 mmol) 1-naphthalen-2-ylmethyl-cyclopropylamine. Yield: 20 mg (5%, trifluoroacetate); mass spectroscopy: $[M+H]^+=405$.

EXAMPLE 15

8-{2-[1-(2,4-dimethyl-benzyl)-cyclopronylamino]-1-hydroxy-ethyl}-5-hydroxy-4H-benzo[1,4]oxazin-3-one

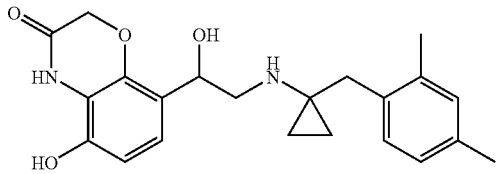

Prepared according to general method 3 from 329 mg (1 mmol) 5-benzyloxy-8-(2,2-dihydroxy-acetyl)-4H-benzo[1,4]oxazin-3-one and 175 mg (1 mmol) 1-(2,4-dimethyl-benzyl)-cyclopropylamine. Yield: 176 mg (36%, trifluoroacetate); mass spectroscopy: $[M+H]^+=383$.

EXAMPLE 16

5-hydroxy-8-{1-hydroxy-2-[1-(2,3,5,6-tetramethyl-benzyl)-cyclopropylamino]-ethyl}-4H-benzo[1,4]oxazin-3-one

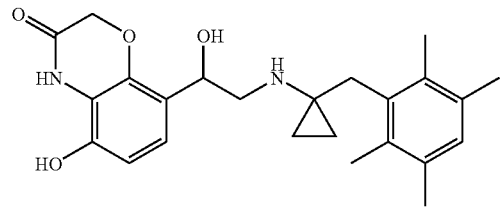

Prepared according to general method 3 from 329 mg (1 mmol) 5-benzyloxy-8-(2,2-dihydroxy-acetyl)-4H-benzo[1,4]oxazin-3-one and 203 mg (1 mmol) 1-(2,3,5,6-tetramethyl-benzyl)-cyclopropylamine. Yield: 93 mg (18%, trifluoroacetate); mass spectroscopy: $[M+H]^+=411$.

EXAMPLE 17

5-hydroxy-8-(1-hydroxy-2-{1-[2-(4-methoxy-phenyl)-ethyl]-cyclopropylamino}-ethyl)-4H-benzo[1,4]oxazin-3-one

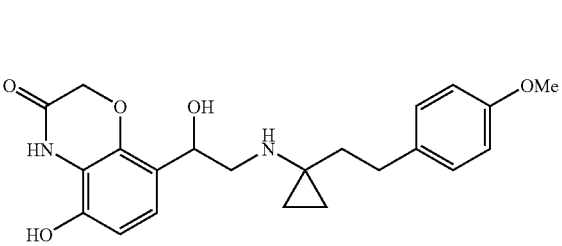

Prepared according to general method 3 from 329 mg (1 mmol) 5-benzyloxy-8-(2,2-dihydroxy-acetyl)-4H-benzo[1,4]oxazin-3-one and 191 mg (1 mmol) 1-[2-(4-methoxy-phenyl)-ethyl]-cyclopropylamine. Yield: 55 mg (11%, trifluoroacetate); mass spectroscopy: $[M+H]^+=399$.

EXAMPLE 18

8-{2-[1-(2,6-difluoro-benzyl)-cyclopropylamino]-1-hydroxy-ethyl}-5-hydroxy-4H-benzo[1,4]oxazin-3-one

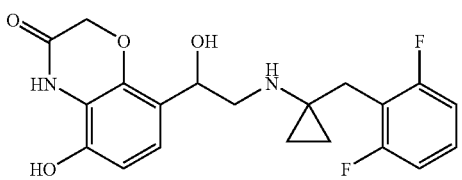

Prepared according to general method 3 from 329 mg (1 mmol) 5-benzyloxy-8-(2,2-dihydroxy-acetyl)-4H-benzo[1,4]oxazin-3-one and 183 mg (1 mmol) 1-(2,6-difluoro-benzyl)-cyclopropylamine. Yield: 108 mg (21%, trifluoroacetate); mass spectroscopy: $[M+H]^+=391$.

EXAMPLE 19

8-{2-[1-(4-amino-benzyl)-cyclopropylamino]-1-hydroxy-ethyl}-5-hydroxy-4H-benzo[1,4]oxazin-3-one

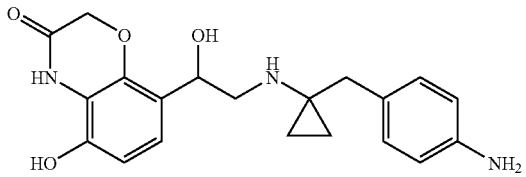

Prepared according to general method 3 from 329 mg (1 mmol) 5-benzyloxy-8-(2,2-dihydroxy-acetyl)-4H-benzo[1,4]oxazin-3-one and 342 mg (1 mmol) [4-(1-amino-cyclopropylmethyl)-phenyl]-dibenzyl-amine. Yield: 49 mg (10%, trifluoroacetate); mass spectroscopy: [M+H]$^+$=370.

EXAMPLE 20

5-hydroxy-8-{1-hydroxy-2-[1-(4-hydroxy-benzyl)-cyclopropylamino]-ethyl}-4H-benzo[1,4]oxazin-3-one

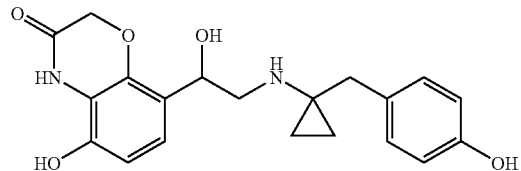

Prepared according to general method 3 from 329 mg (1 mmol) 5-benzyloxy-8-(2,2-dihydroxy-acetyl)-4H-benzo[1,4]oxazin-3-one and 253 mg (1 mmol) 1-(4-benzyloxy-benzyl)-cyclopropylamine. Yield: 20 mg (4%, trifluoroacetate); mass spectroscopy: [M+H]$^+$=371.

EXAMPLE 21

8-{2-[1-(3,4-dimethoxy-benzyl)-cyclopropylamino]-1-hydroxy-ethyl}-5-hydroxy-4H-benzo[1,4]oxazin-3-one

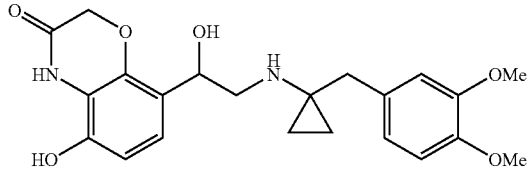

Prepared according to general method 3 from 329 mg (1 mmol) 5-benzyloxy-8-(2,2-dihydroxy-acetyl)-4H-benzo[1,4]oxazin-3-one and 207 mg (1 mmol) 1-(3,4-dimethoxy-benzyl)-cyclopropylamine. Yield: 15 mg (3%, trifluoroacetate); mass spectroscopy: [M+H]$^+$=415.

EXAMPLE 22

8-{2-[1-(4-ethoxy-benzyl)-cyclopropylamino]-1-hydroxy-ethyl}-5-hydroxy-4H-benzo[1,4]oxazin-3-one

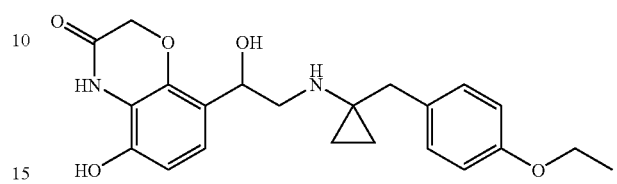

Prepared according to general method 3 from 329 mg (1 mmol) 5-benzyloxy-8-(2,2-dihydroxy-acetyl)-4H-benzo[1,4]oxazin-3-one and 191 mg (1 mmol) 1-(4-ethoxy-benzyl)-cyclopropylamine. Yield: 17 mg (3%, trifluoroacetate); mass spectroscopy: [M+H]$^+$=399.

EXAMPLE 23

8-{2-[1-(4-butoxy-benzyl)-cyclopropylamino]-1-hydroxy-ethyl}-5-hydroxy-4H-benzo[1,4]oxazin-3-one

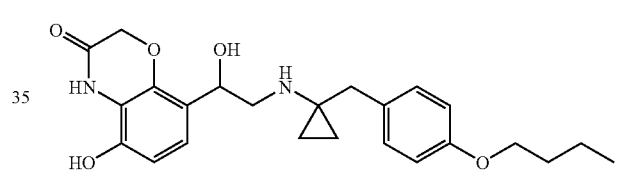

Prepared according to general method 3 from 329 mg (1 mmol) 5-benzyloxy-8-(2,2-dihydroxy-acetyl)-4H-benzo[1,4]oxazin-3-one and 219 mg (1 mmol) 1-(4-butoxy-benzyl)-cyclopropylamine. Yield: 107 mg (20%, trifluoroacetate); mass spectroscopy: [M+H]$^+$=427.

EXAMPLE 24

5-hydroxy-8-{1-hydroxy-2-[1-(2,4,6-trimethyl-benzyl)-cyclopropylamino]-ethyl}-4H-benzo[1,4]oxazin-3-one

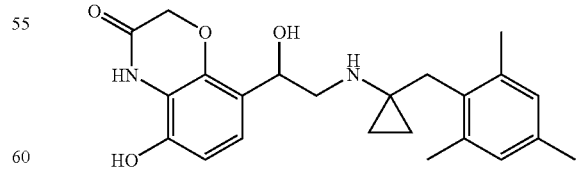

Prepared according to general method 3 from 329 mg (1 mmol) 5-benzyloxy-8-(2,2-dihydroxy-acetyl)-4H-benzo[1,4]oxazin-3-one and 189 mg (1 mmol) 1-(2,4,6-trimethyl-benzyl)-cyclopropylamine. Yield: 26 mg (5%, trifluoroacetate); mass spectroscopy: [M+H]$^+$=397.

EXAMPLE 25

5-hydroxy-8-{1-hydroxy-2-[(1-phenyl-cyclopropyl-methyl)-amino]-ethyl}-4H-benzo[1,4]oxazin-3-one

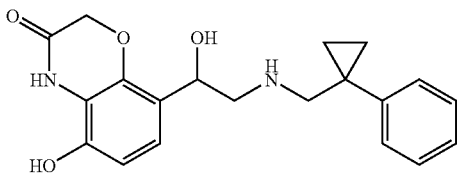

Prepared from 329 mg (1 mmol) 5-benzyloxy-8-(2,2-dihydroxy-acetyl)-4H-benzo[1,4]oxazin-3-one and 147 mg (1 mmol) C-(1-phenyl-cyclopropyl)-methylamine. Final purification by chromatography (silica gel; dichloromethane/methanol gradient). Yield: 30 mg (8%); mass spectroscopy: $[M+H]^+=355$.

EXAMPLE 26

5-hydroxy-8-{1-hydroxy-2-[1-(2-naphthalen-2-yl-ethyl)-cyclopropylamino]-ethyl}-4H-benzo[1,4]oxazin-3-one

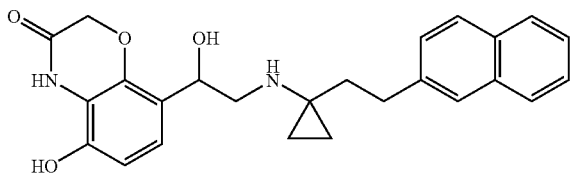

Prepared from 5-benzyloxy-8-(2,2-dihydroxy-acetyl)-4H-benzo[1,4]oxazin-3-one and 1-(2-naphthalen-2-yl-ethyl)-cyclopropylamine. Mass spectroscopy: $[M+H]^+=419$.

General Method 5:

1 mmol of methyl 2-benzyloxy-5-(2-ethoxy-2-hydroxy-acetyl)-benzoate and 1 mmol amine are stirred for 30 minutes in 5 mL tetrahydrofuran at ambient temperature. The mixture is cooled to 0° C. and under an argon atmosphere 1.5 mL of a 2 molar solution of lithium borohydride in tetrahydrofuran are added dropwise. After 30 minutes stirring at ambient temperature a further 1.5 mL of the 2 molar solution of lithium borohydride in tetrahydrofuran are added and the reaction solution is heated to 50° C. for 4 hours. It is combined with 10 mL dichloromethane and 3 mL water, stirred for a further hour and then through filtered kieselguhr, while eluting with dichloromethane. The eluate is evaporated down and the residue is dissolved in methanol and hydrogenated in the presence of palladium on charcoal (10%) at 2.5 bar and ambient temperature. Then the catalyst is separated off and the crude product is purified by chromatography (reverse phase, acetonitrile/water gradient with 0.1% trifluoroacetic acid).

EXAMPLE 27

2-hydroxymethyl-4-{1-hydroxy-2-[(1-phenyl-cyclopropylmethyl)-amino]-ethyl}-phenol

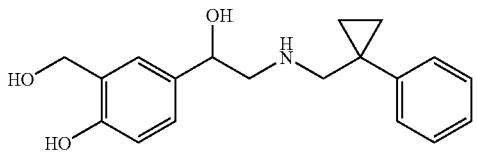

Prepared from 344 mg (1 mmol) methyl 2-benzyloxy-5-(2-ethoxy-2-hydroxy-acetyl)-benzoate and 147 mg (1 mmol) 1-phenyl-cyclopropyl-methylamine. In a departure from General Method 5 the target compound is purified by chromatography on a silica gel column (dichloromethane/methanol gradient).

Yield: 162 mg (52%); mass spectroscopy: $[M+H]^+=314$.

EXAMPLE 28

4-{1-hydroxy-2-[1-(4-methoxy-benzyl)-cyclopropylamino]-ethyl}-2-hydroxymethyl-phenol

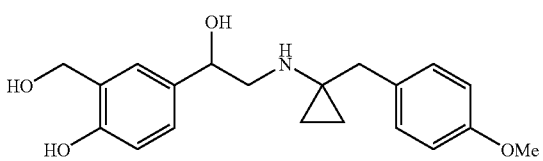

Prepared according to general method 5 from 344 mg (1 mmol) methyl 2-benzyloxy-5-(2-ethoxy-2-hydroxy-acetyl)-benzoate and 177 mg (1 mmol) 1-(4-methoxy-benzyl)-cyclopropylamine. Yield: 123 mg (27%, trifluoroacetate); mass spectroscopy: $[M+H]^+=344$.

EXAMPLE 29

4-[2-(1-benzyl-cyclopropylamino)-1-hydroxy-ethyl]-2-hydroxymethyl-phenol

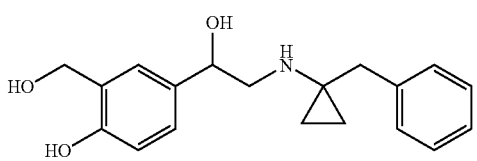

Prepared according to general method 5 from 344 mg (1 mmol) methyl 2-benzyloxy-5-(2-ethoxy-2-hydroxy-acetyl)-benzoate and 147 mg (1 mmol) 1-benzyl-cyclopropylamine. Yield: 184 mg (43%, trifluoroacetate); mass spectroscopy: $[M+H]^+=314$.

EXAMPLE 30

4-{2-[1-(2,6-dimethyl-benzyl)-cyclopropylamino]-1-hydroxy-ethyl}-2-hydroxymethyl-phenol

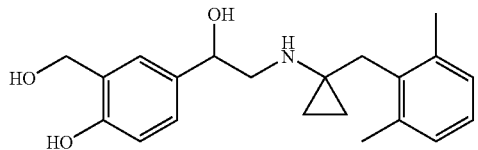

Prepared according to general method 5 from 344 mg (1 mmol) methyl 2-benzyloxy-5-(2-ethoxy-2-hydroxy-acetyl)-benzoate and 175 mg (1 mmol) 1-(2,6-dimethyl-benzyl)-cyclopropylamine. Yield: 64 mg (14%, trifluoroacetate); mass spectroscopy: [M+H]$^+$=342.

EXAMPLE 31

6-hydroxy-8-{1-hydroxy-2-[1-(4-methoxy-benzyl)-cyclopropylamino]-ethyl}-4H-benzo[1,4]oxazin-3-one

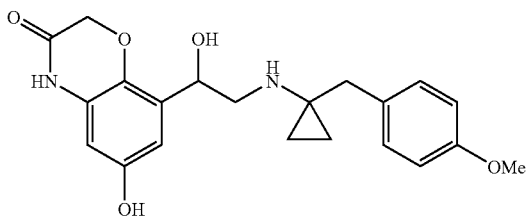

Prepared from 357 mg (1 mmol) 6-benzyloxy-8-(2-ethoxy-2-hydroxy-acetyl)-4H-benzo[1,4]oxazin-3-one and 177 mg (1 mmol) 1-(4-methoxyoxy-benzyl)-cyclopropylamine.
Yield: 109 mg (22%, trifluoroacetate); mass spectroscopy: [M+H]$^+$=385.

EXAMPLE 32

6-hydroxy-8-{1-hydroxy-2-[1-(4-hydroxy-benzyl)-cyclopropylamino]-ethyl}-4H-benzo[1,4]oxazin-3-one

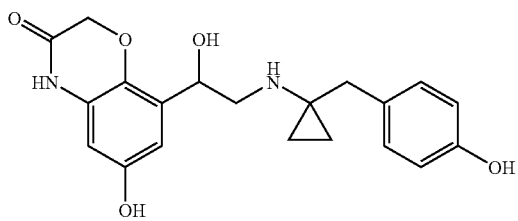

Prepared according to general method 3 from 357 mg (1 mmol) 6-benzyloxy-8-(2-ethoxy-2-hydroxy-acetyl)-4H-benzo[1,4]oxazin-3-one and 253 mg (1 mmol) 1-(4-benzyloxy-benzyl)-cyclopropylamine. Yield: 47 mg (10%, trifluoroacetate); mass spectroscopy: [M+H]$^+$=371.

EXAMPLE 33

6-hydroxy-8-{1-hydroxy-2-[(1-phenyl-cyclopropyl-methyl)-amino]-ethyl}-4H-benzo[1,4]oxazin-3-one

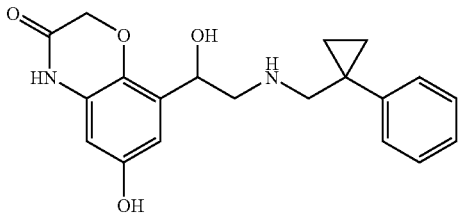

Prepared from 357 mg (1 mmol) 6-benzyloxy-8-(2-ethoxy-2-hydroxy-acetyl)-4H-benzo[1,4]oxazin-3-one and 147 mg (1 mmol) (1-phenyl-cyclopropyl)-methylamine. Yield: 138 mg (39%); mass spectroscopy: [M+H]$^+$=355.

EXAMPLE 34

8-{2-[1-(2,6-dimethyl-benzyl)-cyclopropylamino]-1-hydroxy-ethyl}-6-hydroxy-4H-benzo[1,4]oxazin-3-one

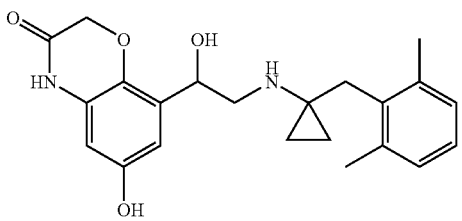

Obtained from 357 mg (1 mmol) 6-benzyloxy-8-(2-ethoxy-2-hydroxy-acetyl)-4H-benzo[1,4]oxazin-3-one and 175 mg (1 mmol) 1-(2,6-dimethyl-benzyl)-cyclopropylamine.
Yield: 93 mg (19%, trifluoroacetate); mass spectroscopy: [M+H]$^+$=383.

EXAMPLE 35

8-{2-[1-(3,5-dimethyl-benzyl)-cyclopropylamino]-1-hydroxy-ethyl}-6-hydroxy-4H-benzo[1,4]oxazin-3-one

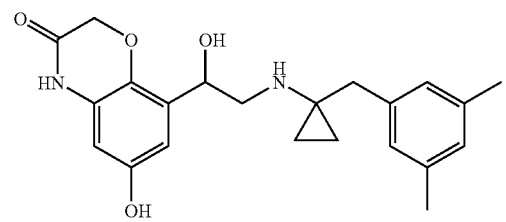

Prepared from 357 mg (1 mmol) 6-benzyloxy-8-(2-ethoxy-2-hydroxy-acetyl)-4H-benzo[1,4]oxazin-3-one and 175 mg (1 mmol) 1-(3,5-dimethyl-benzyl)-cyclopropylamine according to general method 3.

Yield: 155 mg (31%, trifluoroacetate); mass spectroscopy: [M+H]$^+$=383.

EXAMPLE 36

6-hydroxy-8-{1-hydroxy-2-[1-(4-trifluoromethoxy-benzyl)-cyclopropylamino]-ethyl}-4H-benzo[1,4]oxazin-3-one

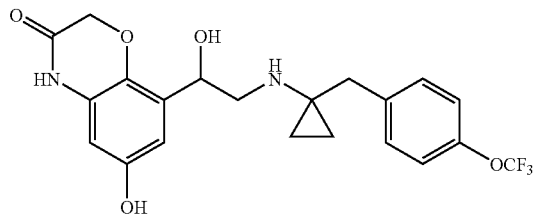

Prepared from 357 mg (1 mmol) 6-benzyloxy-8-(2-ethoxy-2-hydroxy-acetyl)-4H-benzo[1,4]oxazin-3-one and 231 mg (1 mmol) 1-(4-trifluoromethoxy-benzyl)-cyclopropylamine according to general method 3.

Yield: 148 mg (27%, trifluoroacetate); mass spectroscopy: [M+H]$^+$=439.

EXAMPLE 37

8-{2-[1-(2,4-dichloro-benzyl)-cyclopropylamino]-1-hydroxy-ethyl}-6-hydroxy-4H-benzo[1,4]oxazin-3-one

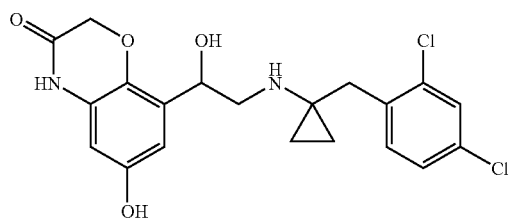

458 mg (0.73 mmol) benzylether are obtained as the trifluoroacetate from the reaction of 357 mg (1 mmol) 6-benzyloxy-8-(2-ethoxy-2-hydroxy-acetyl)-4H-benzo[1,4]oxazin-3-one and 216 mg (1 mmol) 1-(2,4-dichloro-benzyl)-cyclopropylamine. The subsequent debenzylation is carried out according to general method 4 with boron tribromide.

Yield: 158 mg (29% over 2 steps; trifluoroacetate); mass spectroscopy: [M+H]$^+$=423/5/7.

EXAMPLE 38

8-{2-[1-(4-chloro-phenoxymethyl)-cyclopropylamino]-1-hydroxy-ethyl}-6-hydroxy-4H-benzo[1,4]oxazin-3-one

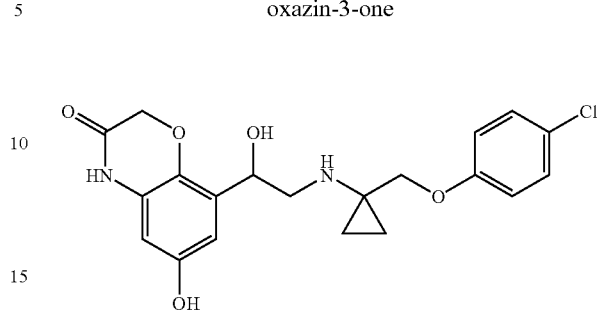

The reaction of 357 mg (1 mmol) 6-benzyloxy-8-(2-ethoxy-2-hydroxy-acetyl)-4H-benzo[1,4]oxazin-3-one and 198 mg (1 mmol) 1-(4-chloro-phenoxymethyl)-cyclopropylamine yields 259 mg (0.4 mmol) benzylether (trifluoroacetate). This is debenzylated according to general method 4 with boron tribromide.

Yield: 99 mg (19% over 2 steps; trifluoroacetate); mass spectroscopy: [M+H]$^+$=405/7.

Examples 39 to 42 are carried out according to general method 3 except that there is no need to cleave the benzyl protective group. The yields given refer in each case to the reaction of 1 mmol of 1-(4-amino-3,5-dichloro-phenyl)-2,2-dihydroxy-ethanone and 1 mmol of amine.

EXAMPLE 39

1-(4-amino-3,5-dichloro-phenyl)-2-[(1-phenyl-cyclopropylmethyl)-amino}-ethanol

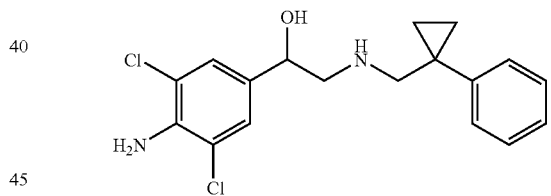

Yield: 63 mg (14%, trifluoroacetate); mass spectroscopy: [M+H]$^+$=351/353/355.

EXAMPLE 40

1-(4-amino-3,5-dichloro-phenyl)-2-[1-(2,6-dimethyl-benzyl)-cyclopropylamino]-ethanol

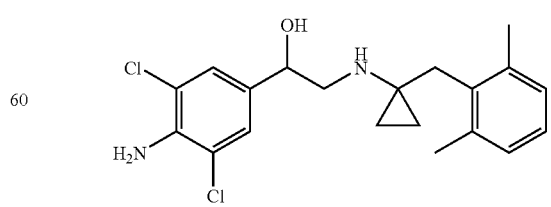

Yield: 101 mg (21%, trifluoroacetate); mass spectroscopy: [M+H]$^+$=379/381/383.

EXAMPLE 41

1-(4-amino-3,5-dichloro-phenyl)-2-[1-(4-methoxy-benzyl)-cyclopropylamino]-ethanol

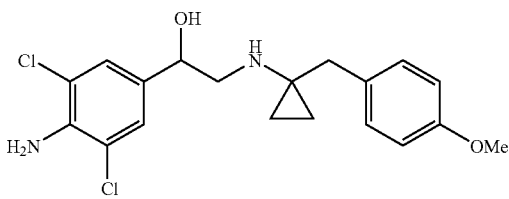

Yield: 167 mg (34%, trifluoroacetate); mass spectroscopy: [M+H]$^+$=381/383/385.

EXAMPLE 42

1-(4-amino-3,5-dichloro-phenyl)-2-(1-benzyl-cyclopropylamino)-ethanol

Yield: 271 mg (58%, trifluoroacetate); mass spectroscopy: [M+H]$^+$=351/353/355.

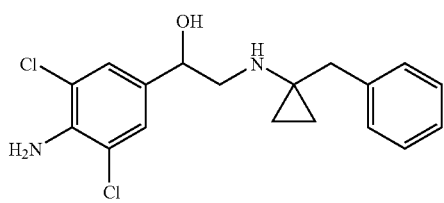

EXAMPLE 43

8-hydroxy-5-{1-hydroxy-2-[1-(4-methoxy-benzyl)-cyclopropylamino]-ethyl}-1H-quinolin-2-one

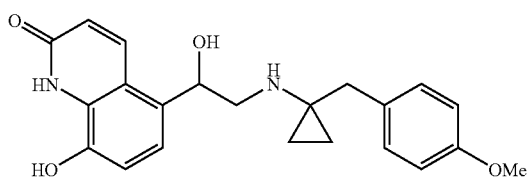

a) 8-benzyloxy-5-{1-hydroxy-2-[1-(4-methoxy-benzyl)-cyclopropylamino]-ethyl}-1H-quinolin-2-one 587 mg (2.0 mmol) 8-benzyloxy-5-oxiranyl-1H-quinolin-2-one and 480 mg (2.7 mmol) 1-(4-methoxy-benzyl)-cyclopropylamine are refluxed in 10 mL n-butanol for 10 hours. Then the solvent is distilled off and the residue is purified by chromatography (reverse phase, water/acetonitrile gradient). Yield: 259 mg (27%); mass spectroscopy: [M+H]$^+$=471.

b) 8-hydroxy-5-{1-hydroxy-2-[1-(4-methoxy-benzyl)-cyclopropylamino]-ethyl}-1H-quinolin-2-one 258 mg (0.51 mmol) 8-benzyloxy-5-{1-hydroxy-2-[1-(4-methoxy-benzyl)-cyclopropylamino]-ethyl}-1H-quinolin-2-one in 10 mL methanol are hydrogenated with palladium on charcoal as catalyst at 3 bar. Then the catalyst is separated off, the solvent is distilled off and the residue is purified by chromatography (reverse phase, water/acetonitrile gradient). Yield: 12 mg (6%); mass spectroscopy: [M+H]$^+$=381.

EXAMPLE 44

8-hydroxy-5-{1-hydroxy-2-[1-(4-trifluoromethyl-benzyl)-cyclopronylamino]-ethyl}-1H-quinolin-2-one

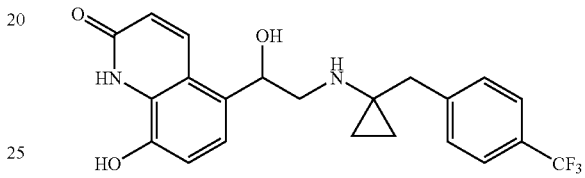

a) 8-benzyloxy-5-{1-hydroxy-2-[1-(4-trifluoromethyl-benzyl)-cyclopropylamino]-ethyl}-1H-quinolin-2-one Reaction of 587 mg (2.0 mmol) 8-benzyloxy-5-oxiranyl-1H-quinolin-2-one and 710 mg (3.3 mmol) 1-(4-trifluoromethyl-benzyl)-cyclopropylamine is carried out analogously to Example 40a43a). Yield: 322 mg (32%); mass spectroscopy: [M+H]$^+$=509.

b) 8-hydroxy-5-{1-hydroxy-2-[1-(4-trifluoromethyl-benzyl)-cyclopropylamino]-ethyl}-1H-quinolin-2-one 322 mg (0.63 mmol) 8-benzyloxy-5-{1-hydroxy-2-[1-(4-trifluoromethyl-benzyl)-cyclopropylamino]-ethyl}-1H-quinolin-2-one are dissolved in 10 mL methanol and hydrogenated in the presence of palladium on charcoal at 3 bar. The precipitated product is dissolved by adding methanol. The catalyst is separated off and the filtrate is evaporated down. The precipitated solid is filtered off and suspended in diethyl ether for further purification. Yield: 161 mg (61%); mass spectroscopy: [M+H]$^+$=419.

General Method 6

7 mmol of the amine present as the hydrochloride are stirred with 1.7 mmol triethylamine for 30 minutes in 6 mL tetrahydrofuran. Then 1.7 mmol glyoxylaldehyde or -acetal is added and the mixture is stirred for a further 1.5 hours. The reaction mixture is cooled to 10° C., combined with 150 mg (6.9 mmol) lithium borohydride, stirred for 30 minutes and then combined with water. Then the mixture is extracted with dichloromethane and the organic phase is dried with sodium sulphate. The solvent is distilled off and the residue is dissolved in ethyl acetate and combined with 10% hydrochloric acid in ethyl acetate. The precipitated solid is filtered off, placed in methanol and hydrogenated with palladium on charcoal at normal pressure. Then the catalyst is separated off and the filtrate is freed from the solvent. By stirring the residue in ethyl acetate or crystallising from the same solvent the product is obtained in the form of a colourless solid.

EXAMPLE 45

6-hydroxy-8-[1-hydroxy-2-(1-phenethyl-cyclohexylamino)-ethyl]-4H-benzo[1,4]oxazin-3-one

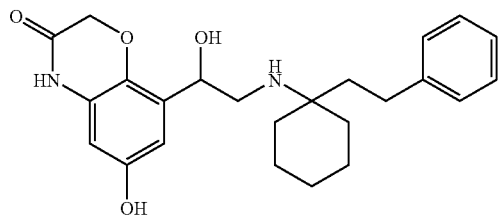

Prepared according to general method 6 from 607 mg (1.70 mmol) 6-benzyloxy-8-(2-ethoxy-2-hydroxy-acetyl)-4H-benzo[1,4]oxazin-3-one and 408 mg (1.70 mmol) 1-phenethylcyclohexylamine hydrochloride.

Yield: 289 mg (38%, hydrochloride), mass spectroscopy: $[M+H]^+=411$.

EXAMPLE 46

8-[2-(1-benzyl-cyclopentylamino)-1-hydroxy-ethyl]-6-hydroxy-4H-benzo[1,4]oxazin-3-one

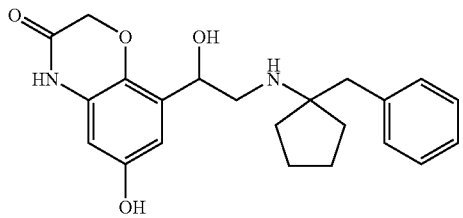

Prepared according to general method 6 from 607 mg (1.70 mmol) 6-benzyloxy-8-(2-ethoxy-2-hydroxy-acetyl)-4H-benzo[1,4]oxazin-3-one and 360 mg (1.70 mmol) 1-benzyl-cyclopentylamine hydrochloride.

Yield: 421 mg (59%, hydrochloride), mass spectroscopy: $[M+H]^+=383$.

EXAMPLE 47

8-{2-[1-(4-fluoro-benzyl)-cyclopentylamino]-1-hydroxy-ethyl}-6-hydroxy-4H-benzo[1,4]oxazin-3-one

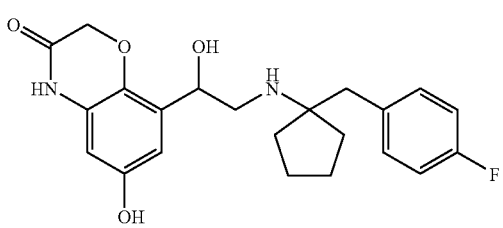

Prepared according to general method 6 from 607 mg (1.70 mmol) 6-benzyloxy-8-(2-ethoxy-2-hydroxy-acetyl)-4H-benzo[1,4]oxazin-3-one and 414 mg (1.70 mmol) 1-(4-fluoro-benzyl)-cyclopentylamine hydrochloride.

Yield: 447 mg (60%, hydrochloride), mass spectroscopy: $[M+H]^+=401$.

EXAMPLE 48

6-hydroxy-8-(1-hydroxy-2-{1-[2-(4-methoxy-phenyl)-ethyl]-cyclohexylamino}-ethyl)-4H-benzo[1,4]oxazin-3-one

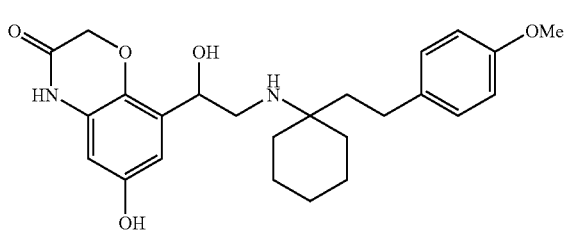

Prepared according to general method 6 from 607 mg (1.70 mmol) 6-benzyloxy-8-(2-ethoxy-2-hydroxy-acetyl)-4H-benzo[1,4]oxazin-3-one and 458 mg (1.70 mmol) 1-[2-(4-methoxy-phenyl)-ethyl]-cyclohexylamine hydrochloride.

Yield: 559 mg (65%, hydrochloride), mass spectroscopy: $[M+H]^+=441$.

EXAMPLE 49

6-hydroxy-8-{1-hydroxy-2-[1-(4-methoxy-benzyl)-cyclopentylamino]-ethyl}-4H-benzo[1,4]oxazin-3-one

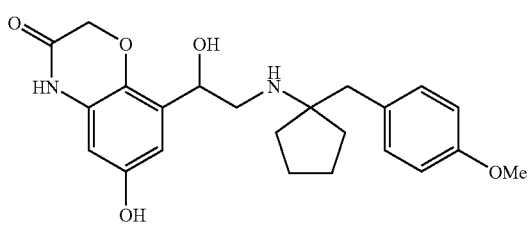

Prepared from 607 mg (1.70 mmol) 6-benzyloxy-8-(2-ethoxy-2-hydroxy-acetyl)-4H-benzo[1,4]oxazin-3-one and 411 mg (1.70 mmol) 1-(4-methoxy-benzyl)-cyclopentylamine hydrochloride according to general method 6.

Yield: 428 mg (56%, hydrochloride). Mass spectroscopy: $[M+H]^+=413$.

EXAMPLE 50

6-hydroxy-8-{1-hydroxy-2-[1-(4-methoxy-benzyl)-cyclohexylamino]-ethyl}-4H-benzo[1,4]oxazin-3-one

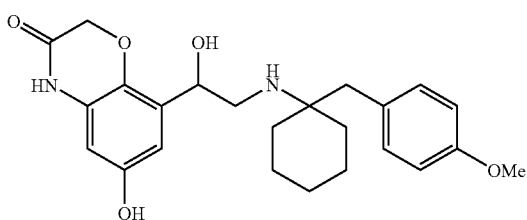

Obtained from 607 mg (1.70 mmol) 6-benzyloxy-8-(2-ethoxy-2-hydroxy-acetyl)-4H-benzo[1,4]oxazin-3-one and 435 mg (1.70 mmol) 1-(4-methoxy-benzyl)-cyclohexylamine hydrochloride according to general method 6.
Yield: 521 mg (66%, hydrochloride). Mass spectroscopy: [M+H]$^+$=427.

EXAMPLE 51

8-(2-{1-[2-(4-fluoro-phenyl)-ethyl]-cyclohexylamino}-1-hydroxy-ethyl)-6-hydroxy-4H-benzo[1,4]oxazin-3-one

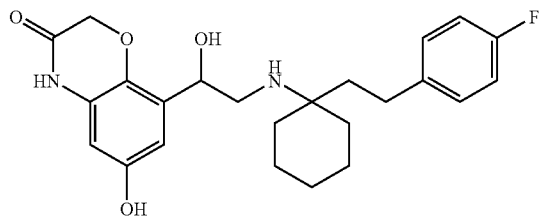

Prepared according to general method 6 from 607 mg (1.70 mmol) 6-benzyloxy-8-(2-ethoxy-2-hydroxy-acetyl)-4H-benzo[1,4]oxazin-3-one and 438 mg (1.70 mmol) 1[2-(4-fluorophenyl)-ethyl]-cyclohexylamine hydrochloride.
Yield: 507 mg (64%, hydrochloride). Mass spectroscopy: [M+H]$^+$=429.

EXAMPLE 52

5-hydroxy-8-[1-hydroxy-2-(1-phenethyl-cyclohexylamino)-ethyl]-4H-benzo[1,4]oxazin-3-one

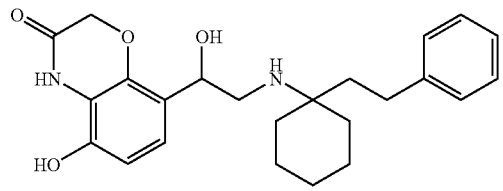

Obtained from 560 mg (1.70 mmol) 5-benzyloxy-8-(2,2-dihydroxy-acetyl)-4H-benzo[1,4]oxazin-3-one and 408 mg (1.70 mmol) 1-phenethylcyclohexylamine hydrochloride according to general method 6.

Yield: 320 mg (42%, hydrochloride). Mass spectroscopy: [M+H]$^+$=411.

EXAMPLE 53

8-[2-(1-benzyl-cyclopentylamino)-1-hydroxy-ethyl]-5-hydroxy-4H-benzo[1,4]oxazin-3-one

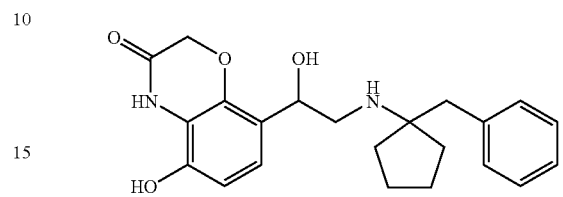

Prepared from 560 mg (1.70 mmol) 5-benzyloxy-8-(2,2-dihydroxy-acetyl)-4H-benzo[1,4]oxazin-3-one and 360 mg (1.70 mmol) 1-benzylcyclopentylamine hydrochloride according to general method 6.
Yield: 328 mg (46%, hydrochloride). Mass spectroscopy: [M+H]$^+$=383.

EXAMPLE 54

8-{2-[1-(4-fluoro-benzyl)-cyclopentylamino]-1-hydroxy-ethyl}-5-hydroxy-4H-benzo[1,4]oxazin-3-one

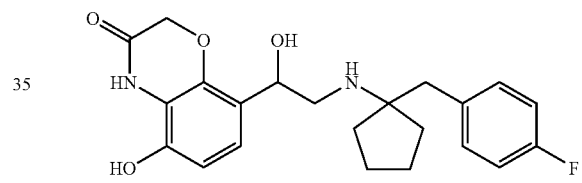

Prepared from 560 mg (1.70 mmol) 5-benzyloxy-8-(2,2-dihydroxy-acetyl)-4H-benzo[1,4]oxazin-3-one and 414 mg (1.70 mmol) 1-(4-fluoro-benzyl)-cyclopentylamine hydrochloride according to general method 6.
Yield: 454 mg (61%, hydrochloride). Mass spectroscopy: [M+H]$^+$=401.

EXAMPLE 55

5-hydroxy-8-(1-hydroxy-2-{1-[2-(4-methoxy-phenyl)-ethyl]-cyclohexylamino}-ethyl)-4H-benzo[1,4]oxazin-3-one

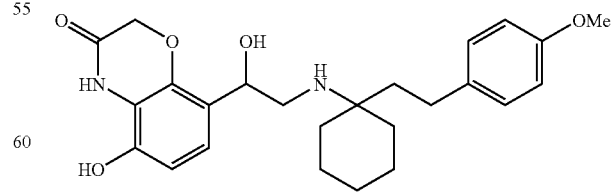

Obtained from 560 mg (1.70 mmol) 5-benzyloxy-8-(2,2-dihydroxy-acetyl)-4H-benzo[1,4]oxazin-3-one and 458 mg (1.70 mmol) 1-[2-(4-methoxy-phenyl)-ethyl]-cyclohexylamine hydrochloride according to general method 6.

Yield: 544 mg (67%, hydrochloride). Mass spectroscopy: [M+H]$^+$=441.

EXAMPLE 56

5-hydroxy-8-{1-hydroxy-2-[1-(4-methoxy-benzyl)-cyclopentylamino]-ethyl}-4H-benzo[1,4]oxazin-3-one

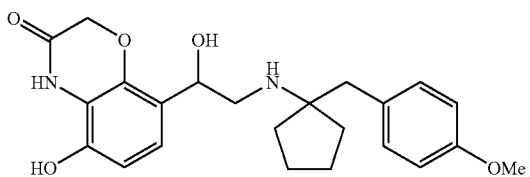

Prepared from 560 mg (1.70 mmol) of 5-benzyloxy-8-(2,2-dihydroxy-acetyl)-4H-benzo[1,4]oxazin-3-one and 411 mg (1.70 mmol) 1-(4-methoxy-benzyl)-cyclopentylamine hydrochloride according to general method 6.

Yield: 467 mg (61%, hydrochloride). Mass spectroscopy: [M+H]$^+$=413.

EXAMPLE 57

5-hydroxy-8-{1-hydroxy-2-[1-(4-methoxy-benzyl)-cyclohexylamino]-ethyl}-4H-benzo[1,4]oxazin-3-one

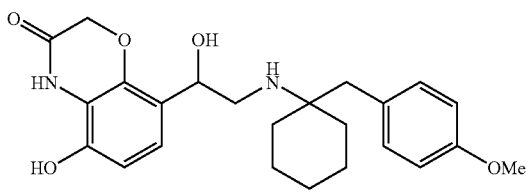

Prepared from 560 mg (1.70 mmol) 5-benzyloxy-8-(2,2-dihydroxy-acetyl)-4H-benzo[1,4]oxazin-3-one and 435 mg (1.70 mmol) 1-(4-methoxy-benzyl)-cyclohexylamine hydrochloride according to general method 6.

Yield: 426 mg (54%, hydrochloride). Mass spectroscopy: [M+H]$^+$=427.

EXAMPLE 58

8-(2-{1-[2-(4-fluoro-phenyl)-ethyl]-cyclohexylamino}-1-hydroxy-ethyl)-5-hydroxy-4H-benzo[1,4]oxazin-3-one

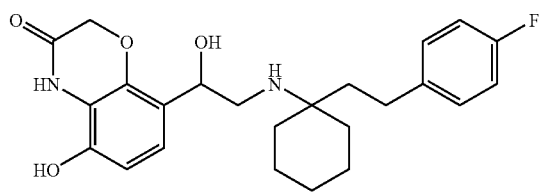

Prepared from 560 mg (1.70 mmol) 5-benzyloxy-8-(2,2-dihydroxy-acetyl)-4H-benzo[1,4]oxazin-3-one and 438 mg (1.70 mmol) 1-[2-(4-fluoro-phenyl)-ethyl]-cyclohexylamine hydrochloride according to general method 6.

Yield: 554 mg (70%, hydrochloride). Mass spectroscopy: [M+H]$^+$=429.

EXAMPLE 59

N-{2-hydroxy-5-[1-hydroxy-2-(1-phenethyl-cyclohexylamino)-ethyl]-phenyl}-methanesulphonamide

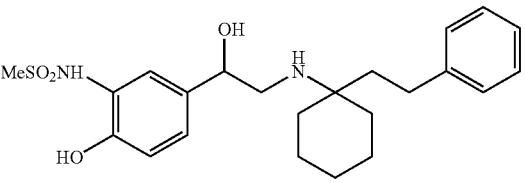

Prepared from 645 mg (1.70 mmol) N-[2-benzyloxy-5-(2-ethoxy-2-hydroxy-acetyl)-phenyl]-methanesulphonamide and 408 mg (1.70 mmol) 1-phenethylcyclohexylamine hydrochloride according to general method 6.

Yield: 336 mg (42%, hydrochloride). Mass spectroscopy: [M+H]$^+$=433.

EXAMPLE 60

N-{5-[2-(1-benzyl-cyclopentylamino)-1-hydroxy-ethyl]-2-hydroxy-phenyl}-methanesulphonamide

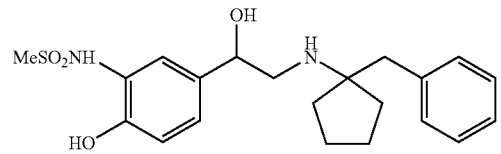

Prepared from 645 mg (1.70 mmol) N-[2-benzyloxy-5-(2-ethoxy-2-hydroxy-acetyl)-phenyl]-methanesulphonamide and 360 mg (1.70 mmol) 1-benzylcyclopentylamine hydrochloride according to general method 6.

Yield: 346 mg (46%, hydrochloride). Mass spectroscopy: [M+H]$^+$=405.

EXAMPLE 61

N-(5-{2-[1-(4-fluoro-benzyl)-cyclopentylamino]-1-hydroxy-ethyl}-2-hydroxy-phenyl)-methanesulphonamide

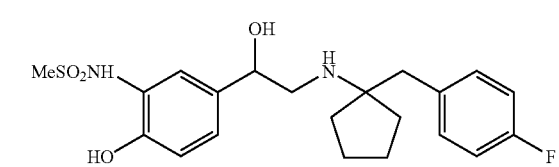

Prepared from 645 mg (1.70 mmol) N-[2-benzyloxy-5-(2-ethoxy-2-hydroxy-acetyl)-phenyl]-methanesulphonamide and 414 mg (1.70 mmol) 1-(4-fluoro-benzyl)-cyclopenty-

EXAMPLE 62

N-[2-hydroxy-5-(1-hydroxy-2-{1-[2-(4-methoxy-phenyl)-ethyl]-cyclohexylamino}-ethyl)-phenyl]-methanesulphonamide

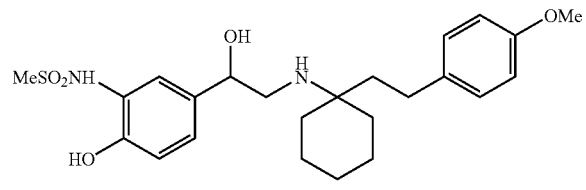

Obtained from 645 mg (1.70 mmol) N-[2-benzyloxy-5-(2-ethoxy-2-hydroxy-acetyl)-phenyl]-methanesulphonamide and 458 mg (1.70 mmol) 1-[2-(4-methoxy-phenyl)-ethyl]-cyclohexylamine hydrochloride according to general method 6. Yield: 544 mg (64%, hydrochloride). Mass spectroscopy: $[M+H]^+=463$.

EXAMPLE 63

N-(2-hydroxy-5-{1-hydroxy-2-[1-(4-methoxy-benzyl)-cyclopentylamino]-ethyl}-phenyl)-methanesulphonamide

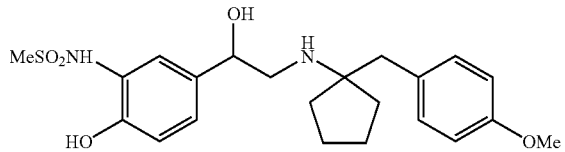

Prepared from 645 mg (1.70 mmol) N-[2-benzyloxy-5-(2-ethoxy-2-hydroxy-acetyl)-phenyl]-methanesulphonamide and 411 mg (1.70 mmol) 1-(4-methoxy-benzyl)-cyclopentylamine hydrochloride according to general method 6. Yield: 369 mg (46%, hydrochloride). Mass spectroscopy: $[M+H]^+=435$.

EXAMPLE 64

N-(2-hydroxy-5-{1-hydroxy-2-[1-(4-methoxy-benzyl)-cyclohexylamino]-ethyl}-phenyl)-methanesulphonamide

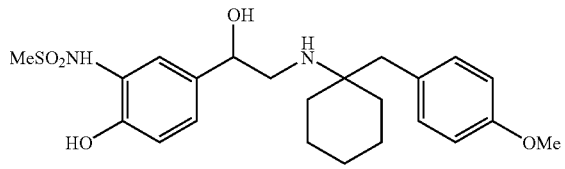

Prepared from 645 mg (1.70 mmol) N-[2-benzyloxy-5-(2-ethoxy-2-hydroxy-acetyl)-phenyl]-methanesulphonamide and 435 mg (1.70 mmol) 1-(4-methoxy-benzyl)-cyclohexylamine hydrochloride according to general method 6.

Yield: 562 mg (68%, hydrochloride). Mass spectroscopy: $[M+H]^+=449$.

EXAMPLE 65

N-[5-(2-{1-[2-(4-fluoro-phenyl)-ethyl]-cyclohexylamino}-1-hydroxy-ethyl)-2-hydroxy-phenyl]-methanesulphonamide

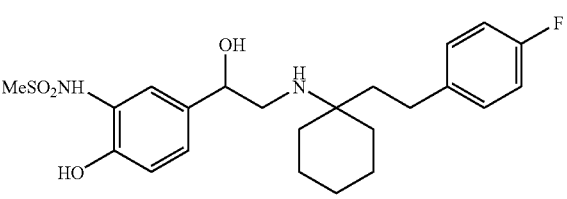

Prepared from 645 mg (1.70 mmol) N-[2-benzyloxy-5-(2-ethoxy-2-hydroxy-acetyl)-phenyl]-methanesulphonamide and 438 mg (1.70 mmol) 1-[2-(4-fluoro-phenyl)-ethyl]-cyclohexylamine hydrochloride according to general method 6.

Yield 614 mg (74%, hydrochloride). Mass spectroscopy: $[M+H]^+=451$.

As has been found, the compounds of formula 1 are characterised by their wide range of applications in the therapeutic field. Particular mention should be made of those applications for which the compounds of formula 1 according to the invention are preferably used on the basis of their pharmaceutical activity as betamimetics.

These include, for example, the treatment of inflammatory and obstructive respiratory complaints, the inhibition of premature labour in midwifery (tocolysis), the restoration of the sinus rhythm in the heart in cases of atrio-ventricular block as well as the correcting of bradycardic heart rhythm disorders (antiarrhythmic agent), the treatment of circulatory shock (vasodilatation and increasing the heart-time volume) as well as the treatment of itching and skin inflammation.

The compounds according to the invention may be used particularly in the treatment of respiratory complaints. In a preferred aspect the present invention therefore relates to the use of compounds of general formula 1 for preparing a pharmaceutical composition for the treatment of respiratory complaints selected from the group comprising obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

The compounds of general formula 1 are preferably used for preparing a pharmaceutical composition for the treatment of obstructive pulmonary diseases selected from among bronchial asthma, paediatric asthma, severe asthma, acute asthma attacks, chronic bronchitis and COPD (chronic obstructive pulmonary disease), while it is particularly preferable according to the invention to use them for preparing a pharmaceutical composition for the treatment of bronchial asthma and COPD.

It is also preferable to use compounds of general formula 1 for preparing a pharmaceutical composition for the treatment of pulmonary emphysema which has its origins in COPD (chronic obstructive pulmonary disease) or α1-proteinase inhibitor deficiency.

It is also preferable to use compounds of general formula 1 for preparing a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

It is also preferable to use compounds of general formula 1 for preparing a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

It is also preferable to use compounds of general formula 1 for preparing a pharmaceutical composition for the treatment of cystic fibrosis or mucoviscidosis.

It is also preferable to use compounds of general formula 1 for preparing a pharmaceutical composition for the treatment of bronchitis, such as for example bronchitis caused by bacterial or viral infection, allergic bronchitis and toxic bronchitis.

It is also preferable to use compounds of general formula 1 for preparing a pharmaceutical composition for the treatment of bronchiectasis.

It is also preferable to use compounds of general formula 1 for preparing a pharmaceutical composition for the treatment of ARDS (adult respiratory distress syndrome).

It is also preferable to use compounds of general formula 1 for preparing a pharmaceutical composition for the treatment of pulmonary oedema, for example toxic pulmonary oedema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

Suitable preparations for administering the compounds of formula 1 include tablets, capsules, suppositories, solutions, powders, etc. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, arabic gum, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations of active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

When the compounds of formula 1 are used, as preferred according to the invention, for the treatment of asthma or COPD, it is particularly preferable to use preparations or pharmaceutical formulations that can be administered by inhalation. Suitable formulations for inhalation include inhalable powders, propellant-driven metered—dose aerosols or propellant-free inhalable solutions. Within the scope of the present invention the term propellant-free inhalable solutions also includes concentrates or sterile ready-to-use inhalable solutions. The formulations which may be used within the scope of the present invention are described in detail in the next part of the specification.

The inhalable powders which may be used according to the invention may contain 1 either on their own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the jig range. The compounds of formula 1 may also be used effectively above the μg range. The dosage may then be in the milligram range, for example.

In another aspect the present invention relates to the above-mentioned pharmaceutical formulations as such, which are characterised in that they contain a compound of formula 1, particularly preferably the above-mentioned pharmaceutical formulations for use by inhalation.

The following formulation examples illustrate the present invention without restricting its scope:

| A) Ampoule solution | |
| --- | --- |
| active substance of formula 1 | 25 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| B) Metered-dose aerosol (suspension) | |
| --- | --- |
| active substance of formula 1 | 0.03 wt. % |
| sorbitolan trioleate | 0.6 wt. % |
| HFA134A:HFA227 2:1 | 99.37 wt. % |

The suspension is poured into a conventional aerosol container with metering valve. Preferably 50 μl suspension are delivered in each puff. The active substance may if desired also be delivered in higher doses.

| C) Metered-dose aerosol (solution) | |
| --- | --- |
| active substance of formula 1 | 0.03 wt. % |
| ethanol abs. | 20 wt. % |
| aqueous HCl 0.01 mol/l | 2.0 wt. % |
| HFA134A | 77.97 wt. % |

The solution is prepared in the conventional manner by mixing the individual constituents.

| D) Inhalable powder | |
| --- | --- |
| active substance of formula 1 | 80 μg |
| lactose monohydrate | ad 10 mg |

The inhalable powder is prepared in the conventional manner by mixing the individual constituents.

The invention claim is:

1. A compound of formula 1a

1a wherein
n denotes 0 or 1;
m denotes 1, 2, 3 or 4;
X denotes a single bond or one of the double-bonded groups $C_2$-$C_6$-alkenylene, —O—$C_1$-$C_6$-alkylene, —NH—$C_1$-$C_6$-alkylene, —S—$C_1$-$C_6$-alkylene or $C_1$-$C_6$-alkylene;
$R^3$ and $R^4$ which may be identical or different denote a group selected from hydrogen, OH, halogen, —$C_1$-$C_6$-alkyl, —$C_1$-$C_6$-haloalkyl, —$C_1$-$C_6$-hydroxyalkyl, $NH_2$, NH(—$C_1$-$C_4$-alkyl) and N(—$C_1$-$C_4$-alkyl)$_2$;
$R^5$, $R^6$, $R^7$ and $R^8$, which may be identical or different, denote hydrogen, $OR^9$, —$C_1$-$C_6$-alkyl, —$C_1$-$C_6$-haloalkyl, —$C_1$-$C_6$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$ or halogen, or
two of the groups $R^5$, $R^6$, $R^7$ and $R^8$, if they are located vicinally to the substituting phenyl ring, together form a double-bonded group selected from $C_2$-$C_6$-alkylene, $C_2$-$C_6$-alkenylene and —O—$C_1$-$C_6$-alkylene-O— wherein in each case one or 2 hydrogen atoms may be replaced by one or two groups selected from —$C_1$-$C_4$-alkyl, —$C_1$-$C_4$-alkoxy, OH, or halogen;
$R^9$ denotes hydrogen, $C_1$-$C_4$-alkyl, $C_6$-$C_{10}$-aryl or $C_6$-$C_{10}$-aryl-$C_1$-$C_4$-alkylene;
$R^{10}$ and $R^{11}$ which may be identical or different, denote hydrogen, $C_1$-$C_4$-alkyl, $C_6$-$C_{10}$-aryl or $C_6$-$C_{10}$-aryl-$C_1$-$C_4$-alkylene;
$R^{12}$ denotes $C_1$-$C_4$-alkyl, $C_6$-$C_{10}$-aryl or $C_6$-$C_{10}$-aryl-$C_1$-$C_4$-alkylene,
optionally in the form of the individual optical isomers, mixtures of the individual enantiomers or racemates, in the form of the free bases or the corresponding acid addition salts thereof with pharmacologically acceptable acids.

2. The compound of formula 1a according to claim 1, wherein
n denotes 0 or 1;
m denotes 1, 2, 3 or 4;
X denotes a single bond or one of the double-bonded groups $C_2$-$C_4$-alkenylene, —O—$C_1$-$C_4$-alkylene, —NH—$C_1$-$C_4$-alkylene, —S—$C_1$-$C_4$-alkylene or $C_1$-$C_4$-alkylene;
$R^3$ and $R^4$ which may be identical or different denote a group selected from hydrogen, OH, halogen, —$C_1$-$C_4$-alkyl, —$C_1$-$C_4$-haloalkyl, —$C_1$-$C_4$-hydroxyalkyl, $NH_2$, NH(—$C_1$-$C_4$-alkyl) and N(—$C_1$-$C_4$-alkyl)$_2$;
$R^5$, $R^6$, $R^7$ and $R^8$, which may be identical or different, denote hydrogen, $OR^9$, —$C_1$-$C_4$-alkyl, —$C_1$-$C_4$-haloalkyl, —$C_1$-$C_4$-hydroxyalkyl, —$C_3$-$C_6$-cycloalkyl, —$C_3$-$C_6$-hydroxycycloalkyl, —CN, $NO_2$, —$COR^9$, —$COOR^9$, —$CONR^{10}R^{11}$, —$NR^{10}R^{11}$, —$NR^{10}COR^9$, —$NR^{10}SO_2R^{12}$, —$SR^{12}$, —$SOR^{12}$, —$SO_2R^{12}$, —$SO_2NR^{10}R^{11}$, fluorine, chlorine or bromine, or two of the groups $R^5$, $R^6$, $R^7$ and $R^8$, if they are located vicinally to the substituting phenyl ring, together form a double-bonded group selected from $C_2$-$C_4$-alkylene, $C_2$-$C_4$-alkenylene and —O—$C_1$-$C_4$-alkylene-O— wherein in each case one or 2 hydrogen atoms may be replaced by one or two groups selected from methyl, methoxy, OH, fluorine, chlorine or bromine;

$R^9$ denotes hydrogen, methyl, ethyl, phenyl, naphthyl, benzyl, naphthylmethyl or 2-phenylethyl;

$R^{10}$ and $R^{11}$ which may be identical or different, denote hydrogen, methyl, ethyl, phenyl, naphthyl, naphthylmethyl, benzyl or 2-phenylethyl;

$R^{12}$ denotes methyl, ethyl, phenyl, naphthyl, naphthylmethyl, benzyl or 2-phenylethyl, optionally in the form of the individual optical isomers, mixtures of the individual enantiomers or racemates, in the form of the free bases or the corresponding acid addition salts thereof with pharmacologically acceptable acids.

3. The compound of formula 1a according to claim 1, wherein n denotes 0 or 1;

m denotes 1, 2, 3 or 4;

X denotes a single bond or one of the double-bonded groups —$CH_2$, —$CH_2$—$CH_2$, —$CH_2$—$CH_2$-$CH_2$, —CH=CH, —$CH_2$—CH=CH, —$CH_2$—O, —$CH_2$—$CH_2$—O, —$CH_2$—$NH_2$, —$CH_2$—$CH_2$—$NH_2$—;

$R^3$ and $R^4$ which may be identical or different denote a group selected from hydrogen, OH, fluorine, chlorine, bromine, methyl, ethyl, —$CH_2F$, —$CHF_2$, —$CF_3$, —$CH_2$—$CH_2$—OH, —$CH_2$—OH, $NH_2$, NH(methyl) and N(methyl)$_2$;

$R^5$, $R^6$, $R^7$ and $R^8$, which may be identical or different, denote hydrogen, OH, methyl, ethyl, propyl, butyl, —$CH_2F$, —$CHF_2$, —$CF_3$, —$CH_2$—$CH_2F$, —$CH_2$—$CHF_2$, —$CH_2$—$CF_3$, —$CH_2$—$CH_2$—OH, —$CH_2$—OH, cyclpropyl, cyclobutyl, cyclopentyl, HO-cyclpropyl, HO-cyclobutyl, HO-cyclopentyl, —CN, $NO_2$, —COphenyl, —COOmethyl, —COOethyl, —$CONH_2$, —CONHmethyl, —CONHphenyl, —CONHbenzyl, —CON(methyl)$_2$, $NH_2$, NH(methyl), N(methyl)$_2$, —NHCOmethyl, —NHCOphenyl, —$NHSO_2$methyl, —$NHSO_2$phenyl, —$NHSO_2$-phenyl-$CH_3$, —$SO_2$methyl, —$SO_2$-phenyl, —$SO_2$-phenyl-$CH_3$, —$SO_2NH_2$, fluorine, chlorine or bromine, or two of the groups $R^5$, $R^6$, $R^7$ and $R^8$, if they are located vicinally to the substituting phenyl ring, together form a double-bonded group selected from —$CH_2$—$CH_2$—$CH_2$, —$CH_2$—$CH_2$—$CH_2$—$CH_2$, —$CH_2$—CH=CH, —CH=CH—CH=CH, —O—$CH_2$—O— and —O—$CH_2$—$CH_2$—O— wherein in each case one or 2 hydrogen atoms may be replaced by one or two groups selected from among methyl, methoxy, OH or fluorine, optionally in the form of the individual optical isomers, mixtures of the individual enantiomers or racemates, in the form of the free bases or the corresponding acid addition salts thereof with pharmacologically acceptable acids.

4. The compound of formula 1a according to claim 1, wherein

X denotes a single bond or one of the double-bonded groups —$CH_2$, —$CH_2CH_2$, —$CH_2$—O, —O—$CH_2$— and —$CH_2$;

and wherein the groups $R^3$, $R^4$, $R^5$, $R^6$, $R^7$, $R^8$, n and m may have the meanings given in claims 1 to 3, optionally in the form of the individual optical isomers, mixtures of the individual enantiomers or racemates, in the form of the free bases or the corresponding acid addition salts thereof with pharmacologically acceptable acids.

5. The compound of formula 1a according claim 1, wherein the groups $R^3$, $R^4$, $R^5$, $R^6$, $R^7$, $R^8$, n, m and X may have the meanings given in claims 1 to 3, optionally in the form of the individual optical isomers, mixtures of the individual enantiomers or racemates, in the form of the free bases or the corresponding acid addition salts thereof with pharmacologically acceptable acids.

6. The compound of formula 1a according to claim 1, wherein $R^3$ and $R^4$ which may be identical or different denote a group selected from hydrogen, OH, fluorine, chlorine, bromine, methyl, ethyl, $CHF_2$, $CH_2F$, $CF_3$, —$CH_2$—$CH_2$—OH, —$CH_2$—OH, $NH_2$, NHmethyl, NHethyl, N(methyl)$_2$ and N(ethyl)$_2$, and wherein the groups $R^1$, $R^2$, $R^5$, $R^6$, $R^7$, $R^8$, n, m and X may have the meanings given in claims 1 to 3, optionally in the form of the individual optical isomers, mixtures of the individual enantiomers or racemates, in the form of the free bases or the corresponding acid addition salts thereof with pharmacologically acceptable acids.

7. The compound of formula 1a according to claim 1, wherein $R^5$, $R^6$, $R^7$ and $R^8$, which may be identical or different, denote hydrogen, OH, methyl, ethyl, propyl, butyl, $CHF_2$, $CH_2F$, $CF_3$, —$CH_2$—$CH_2$—OH, —$CH_2$—OH, methyloxy, ethyloxy, propyloxy, butyloxy, cyclopropyl, hydroxycyclopropyl, $NH_2$, NHmethyl, N(methyl)$_2$, fluorine, chlorine or bromine, or two of the groups $R^5$, $R^6$, $R^7$ and $R^8$, if they are located vicinally to the substituting phenyl ring, denote the double-bonded group —CH=CH—CH=CH— wherein in each case one or 2 hydrogen atoms may be replaced by one or two groups selected from methyl, methoxy, OH, fluorine, chlorine or bromine, and wherein the groups $R^3$, $R^4$ n, m and X may have the meanings given in claim 1, optionally in the form of the individual optical isomers, mixtures of the individual enantiomers or racemates, in the form of the free bases or the corresponding acid addition salts thereof with pharmacologically acceptable acids.

8. The compound of formula 1a according to claim 1, wherein $R^5$, $R^6$, $R^7$ and $R^8$, which may be identical or different, denote hydrogen, OH, methyl, ethyl, propyl, butyl, $CHF_2$, $CH_2F$, $CF_3$, methyloxy, ethyloxy, propyloxy, butyloxy, cyclopropyl, hydroxycyclopropyl, $NH_2$, fluorine, chlorine or bromine, and wherein the groups $R^3$, $R^4$ n, m and X may have the meanings given in claim 1, optionally in the form of the individual optical isomers, mixtures of the individual enantiomers or racemates, in the form of the free bases or the corresponding acid addition salts thereof with pharmacologically acceptable acids.

9. The compound of formula 1a according to claim 1, wherein n denotes 0 or 1;

m denotes 1, 2, 3 or 4;

X denotes a single bond or one of the double-bonded groups —$CH_2$, —$CH_2CH_2$, —$CH_2$—O, —O—$CH_2$— and —$CH_2$;

R³ denotes hydrogen;

R⁴ denotes OH;

R⁵, R⁶, R⁷ and R⁸, which may be identical or different, denote hydrogen, OR⁹, —C₁-C₄-alkyl, —C₁-C₄-haloalkyl, —C₁-C₄-hydroxyalkyl, —C₃-C₆-cycloalkyl, —C₃-C₆-hydroxycycloalkyl, —CN, NO₂, —COR⁹, —COOR⁹, —CONR¹⁰R¹¹, —NR¹⁰R¹¹, —NR¹⁰COR⁹, —NR¹⁰SO₂R¹², —SR¹², —SOR¹², —SO₂R¹², —SO₂NR¹⁰R¹¹, fluorine, chlorine or bromine, or two of the groups R⁵, R⁶, R⁷ and R⁸, if they are located vicinally to the substituting phenyl ring, together form a double-bonded group selected from C₂-C₄-alkylene, C₂-C₄-alkenylene and —O—C₁-C₄-alkylene-O— wherein in each case one or 2 hydrogen atoms may be replaced by one or two groups selected from among methyl, methoxy, OH, fluorine, chlorine or bromine;

R⁹ denotes hydrogen, methyl, ethyl, phenyl, naphthyl, benzyl, naphthylmethyl or 2-phenylethyl;

R¹⁰ and R¹¹ which may be identical or different, denote hydrogen, methyl, ethyl, phenyl, naphthyl, naphthylmethyl, benzyl or 2-phenylethyl;

R¹² denotes methyl, ethyl, phenyl, naphthyl, naphthylmethyl, benzyl or 2-phenylethyl, optionally in the form of the individual optical isomers, mixtures of the individual enantiomers or racemates, in the form of the free bases or the corresponding acid addition salts thereof with pharmacologically acceptable acids.

10. The compound of formula 1a according to claim 1, wherein n denotes 0 or 1;

m denotes 1, 2, 3 or 4;

X denotes a single bond or one of the double-bonded groups —CH₂, —CH₂—CH₂, —CH₂—CH₂-CH₂, —CH=CH, —CH₂—CH=CH, —CH₂—O, —CH₂—CH₂—O, —CH₂—NH₂, —CH₂—CH₂—NH₂—, —O—CH₂— and —CH₂;

R³ denotes hydrogen;

R⁴ denotes hydrogen, fluorine, methyl, OH or CF₃;

R⁵ and R⁸ which may be identical or different, denote hydrogen, methyl, methyloxy or fluorine;

R⁶ and R⁷ which may be identical or different, denote hydrogen, OH, methyl, ethyl, CF₃, methyloxy, ethyloxy, propyloxy, butyloxy, cyclopropyl, hydroxycyclopropyl, NH₂ or fluorine, or R⁶ and R⁷, if they are located vicinally to the substituting phenyl ring, together form the double-bonded group —CH=CH—CH=CH— wherein in each case one or 2 hydrogen atoms may be replaced by one or two groups selected from methyl, methoxy, OH, fluorine, chlorine and bromine, optionally in the form of the individual optical isomers, mixtures of the individual enantiomers or racemates, in the form of the free bases or the corresponding acid addition salts thereof with pharmacologically acceptable acids.

11. The compound of formula 1a according to claims 1, characterised in that it is an enantiomer of formula R-1a,

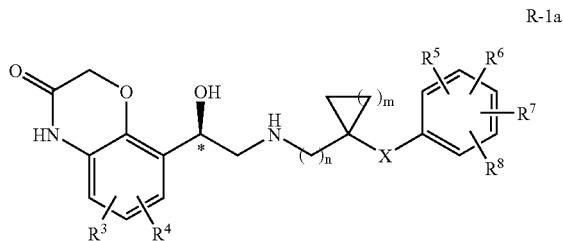

R-1a wherein the groups R³, R⁴, R⁵, R⁶, R⁷, R⁸, n, m and X may have the meanings given in claim 1.

12. A pharmaceutical composition comprising a compound of formula 1a according to claim 1 and pharmaceutically acceptable carriers or excipients thereof.

13. A method of treating a respiratory complaints selected from among bronchial asthma, paediatric asthma, severe asthma, acute asthma attacks and chronic obstructive pulmonary disease, comprising administering to a patient in need thereof a therapeutically effective amount of a compound of formula 1a according to claim 1.

14. The pharmaceutical composition according to claim 12, which is administered via inhalation.

* * * * *